（12）United States Patent
Morioka et al.

(10) Patent No.: US 9,418,778 B2
(45) Date of Patent: Aug. 16, 2016

(54) METHOD OF MANUFACTURING A FEEDTHROUGH

(71) Applicants: Kyocera Corporation, Kyoto (JP); Medtronic, Inc., Minneapolis, MN (US)

(72) Inventors: Kengo Morioka, San Diego, CA (US); Keiichi Fujii, San Jose, CA (US); Arne Knudsen, San Diego, CA (US); Shingo Satou, Kirishima (JP); Hidekazu Otomaru, Kagoshima (JP); Hiroshi Makino, Kirishima (JP); Andrew Thom, Maple Grove, MN (US); Markus Reiterer, Plymouth, MN (US); Gordon Munns, Stacy, MN (US); Thomas Miltich, Otsego, MN (US); Joyce Yamamoto, Maple Grove, MN (US)

(73) Assignees: MEDTRONIC, INC., Minneapolis, MN (US); KYOCERA CORPORATION, Kyoto (JP)

( * ) Notice: Subject to any disclaimer, the term of this patent is extended or adjusted under 35 U.S.C. 154(b) by 0 days.

(21) Appl. No.: 14/203,241

(22) Filed: Mar. 10, 2014

(65) Prior Publication Data

US 2014/0305694 A1    Oct. 16, 2014

Related U.S. Application Data

(63) Continuation of application No. 13/196,695, filed on Aug. 2, 2011, now Pat. No. 8,670,829.

(51) Int. Cl.
*H05K 3/34* (2006.01)
*H01B 17/30* (2006.01)
*A61N 1/375* (2006.01)

(52) U.S. Cl.
CPC .............. *H01B 17/30* (2013.01); *A61N 1/3754* (2013.01); *Y10T 29/49117* (2015.01)

(58) Field of Classification Search
CPC ............... A61N 1/3754; H01B 17/30; Y10T 29/49117; Y10T 29/49126; Y10T 29/49128; Y10T 29/49144
USPC ............ 29/25.02, 25.41, 830–832, 840, 846, 29/851, 852; 174/262; 607/2, 37
See application file for complete search history.

(56) References Cited

U.S. PATENT DOCUMENTS 4,991,582 A * 2/1991 Byers et al. .................. 607/2
5,434,358 A 7/1995 Glahn et al.
(Continued)

FOREIGN PATENT DOCUMENTS

EP    1688160    8/2006
JP    05-334911    12/1993
(Continued)

OTHER PUBLICATIONS

Communication from USPTO regarding Third Party Submission under 37 C.F.R. 1.290 regarding U.S. Appl. No. 13/196,683 (mailed Sep. 19, 2013).
(Continued)

*Primary Examiner* — Donghai D Nguyen
(74) *Attorney, Agent, or Firm* — Foley & Lardner LLP

(57) ABSTRACT

A hermetic feedthrough for an implantable medical device includes an insulator, a conduit configured to conduct electricity through the insulator, and a ferrule coupled to the insulator. The insulator is formed from a ceramic material and the conduit and insulator have a co-fired bond therebetween, which hermetically seals the conduit with the insulator. The insulator is elongate and has opposing ends that include flat surfaces and the ferrule includes a frame for receiving the insulator.

15 Claims, 14 Drawing Sheets

(56) References Cited

U.S. PATENT DOCUMENTS

| | | |
|---|---|---|
| 5,559,056 A | 9/1996 | Weiler |
| 5,620,476 A | 4/1997 | Truex et al. |
| 5,782,891 A | 7/1998 | Hassler et al. |
| 5,817,984 A | 10/1998 | Taylor et al. |
| 5,855,995 A | 1/1999 | Haq et al. |
| 6,059,601 A | 5/2000 | Hirai et al. |
| 6,414,835 B1 | 7/2002 | Wolf et al. |
| 6,516,808 B2 | 2/2003 | Schulman |
| 6,586,675 B1 | 7/2003 | Bealka et al. |
| 6,618,623 B1 | 9/2003 | Pless |
| 7,164,572 B1 | 1/2007 | Burdon et al. |
| 7,174,223 B2 | 2/2007 | Dalton et al. |
| 7,211,103 B2 | 5/2007 | Greenberg et al. |
| 7,310,216 B2 | 12/2007 | Stevenson et al. |
| 7,630,768 B1 | 12/2009 | Coffed et al. |
| 7,668,597 B2 * | 2/2010 | Engmark et al. .............. 607/37 |
| 7,988,507 B2 | 8/2011 | Darley et al. |
| 8,000,804 B1 | 8/2011 | Wessendorf et al. |
| 8,160,707 B2 | 4/2012 | Iyer et al. |
| 8,258,635 B2 | 9/2012 | Greenberg et al. |
| 8,494,636 B2 | 7/2013 | Smith et al. |
| 2002/0166618 A1 | 11/2002 | Wolf et al. |
| 2003/0082958 A1 | 5/2003 | Robinson et al. |
| 2004/0068302 A1 | 4/2004 | Rodgers et al. |
| 2004/0116976 A1 | 6/2004 | Spadgenske |
| 2004/0267107 A1 | 12/2004 | Lessar et al. |
| 2005/0007718 A1 | 1/2005 | Stevenson et al. |
| 2006/0247734 A1 | 11/2006 | Greenberg et al. |
| 2006/0259093 A1 | 11/2006 | Stevenson et al. |
| 2006/0282126 A1 | 12/2006 | Fischbach et al. |
| 2006/0283624 A1 | 12/2006 | Ok et al. |
| 2007/0041164 A1 | 2/2007 | Greenberg et al. |
| 2007/0060969 A1 | 3/2007 | Burdon et al. |
| 2007/0060970 A1 | 3/2007 | Burdon et al. |
| 2007/0096281 A1 | 5/2007 | Greenberg et al. |
| 2007/0179553 A1 | 8/2007 | Iyer et al. |
| 2007/0179554 A1 | 8/2007 | Iyer et al. |
| 2007/0217121 A1 | 9/2007 | Fu et al. |
| 2007/0236861 A1 | 10/2007 | Burdon et al. |
| 2008/0208289 A1 | 8/2008 | Darley et al. |
| 2008/0269623 A1 | 10/2008 | Ruben |
| 2008/0314502 A1 | 12/2008 | Ok et al. |
| 2009/0079518 A1 | 3/2009 | Iyer |
| 2009/0236141 A1 | 9/2009 | Kim et al. |
| 2011/0029036 A1 | 2/2011 | Yamamoto et al. |
| 2011/0041330 A1 | 2/2011 | Kumar et al. |
| 2011/0048770 A1 | 3/2011 | Reiterer et al. |
| 2011/0106228 A1 | 5/2011 | Reiterer |
| 2011/0226304 A1 | 9/2011 | Hayashi et al. |

FOREIGN PATENT DOCUMENTS

| | | |
|---|---|---|
| JP | 2010-109069 | 5/2010 |
| JP | 2010-177482 | 8/2010 |
| JP | 2011-091411 | 5/2011 |
| WO | WO 97/38752 | 10/1997 |
| WO | WO 2010/141100 | 12/2010 |
| WO | WO 2011/025667 | 3/2011 |
| WO | WO-2011/025667 | 3/2011 |

OTHER PUBLICATIONS

International Search Report and Written Opinion for Application No. PCT/US2012/048161 mailed Oct. 17, 2012 (10 pages).

Third Party Submission under 37 C.F.R. 1.290 regarding U.S. Appl. No. 13/196,683 (submitted Sep. 17, 2013).

Office Action issued by the U.S. Patent and Trademark Office in U.S. Appl. No. 13/196,698, dated Nov. 20, 2015.

* cited by examiner

METHOD OF MANUFACTURING A FEEDTHROUGH

CROSS-REFERENCE TO RELATED APPLICATIONS

This application is a Continuation of U.S. patent application Ser. No. 13/196,695, filed Aug. 2, 2011, which is incorporated by reference herein in its entirety.

BACKGROUND

Technology disclosed herein relates generally to the field of feedthroughs serving as an electrical interface to connect portions of a circuit on opposite sides of a barrier. More specifically, technology disclosed herein relates to hermetic feedthroughs for use with implantable medical devices that are constructed through a co-firing process with a combination of materials selected to be both biocompatible and biostable over a long duration.

SUMMARY

One embodiment relates to a hermetic feedthrough for an implantable medical device, which includes an insulator, a conduit configured to conduct electricity through the insulator, and a ferrule coupled to the insulator. The insulator is formed from a ceramic material. The conduit and insulator have a co-fired bond therebetween, which hermetically seals the conduit with the insulator. The insulator is elongate and has opposing ends that include flat surfaces and the ferrule includes a frame for receiving the insulator.

Another embodiment relates to a feedthrough, which includes an insulator and a conduit configured to conduct electricity through the insulator. The insulator is formed from a ceramic material and has a top, a bottom, two sides extending lengthwise along the insulator, and two sides on ends of the insulator. The conduit is configured to conduct electricity between the top and bottom of the insulator. The two sides on the ends of the insulator comprise flat surfaces.

Yet another embodiment relates to a method of manufacturing a feedthrough. The method includes co-firing a structure that includes a material, which is an electrical insulator, and a conduit configured to conduct electricity through the electrical insulator. The method further includes cutting the structure to form the feedthrough, where the feedthrough has a top, a bottom, two sides extending lengthwise along the insulator, and two sides on ends of the insulator. The two sides on the ends of the insulator comprise flat surfaces. The method still further includes rounding corners between the two sides extending lengthwise along the insulator and the two sides on the ends of the insulator.

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 1:
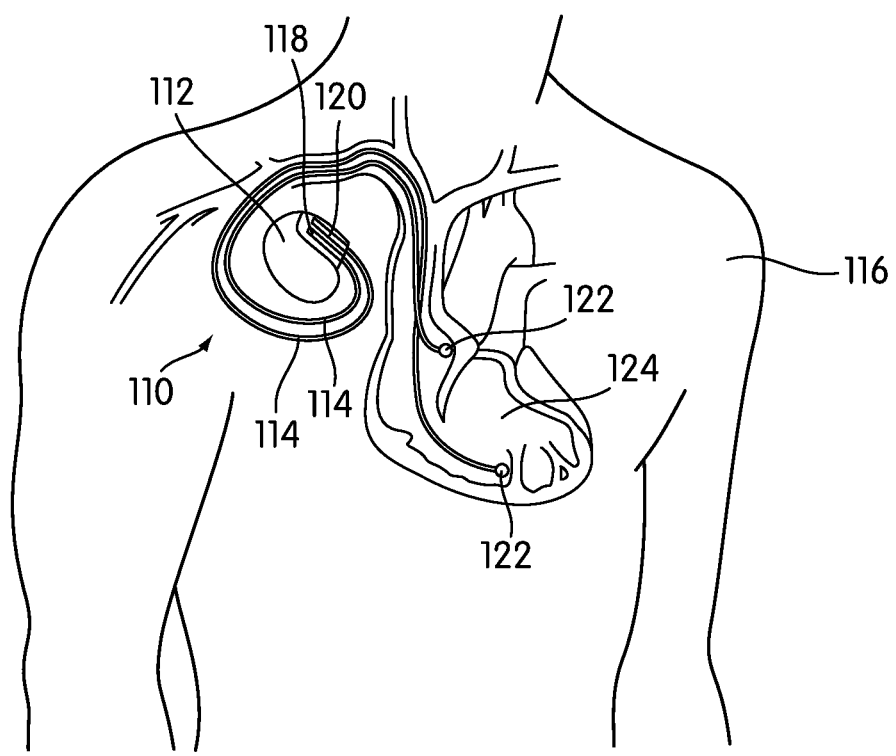
FIG. 1 is a schematic view of a medical device implanted within a patient according to an exemplary embodiment.

Referring to FIG. 1, an implantable medical device 110, such as a pacemaker or a defibrillator, includes a base 112 (e.g., pulse generator, main body) and leads 114. The device 110 may be implanted in a human patient 116 or other being. In some embodiments, the device 110 is configured to provide a therapeutic treatment in the form of an electrical pulse, which in some embodiments may be on the order of about 700 volts. In contemplated embodiments, the device 110, or a variation thereof, may be used to treat or monitor a wide range of conditions such as pain, incontinence, hearing loss, movement disorders including epilepsy and Parkinson's disease, sleep apnea, and a variety of other physiological, psychological, and emotional conditions and disorders.

Within the base 112, the device 110 may include components, such as control circuitry and energy storage devices (e.g., secondary battery, capacitor), that may not be biocompatible or able to function when wet. However, according to an exemplary embodiment, the base 112 is hermetically-sealed and formed with an exterior of a biocompatible and biostable material (e.g., titanium, biocompatible coating) isolating the interior of the base 112 from bodily fluids of the patient 116 that are outside the base 112. In some embodiments, the base 112 further includes a hermetic feedthrough 118 (e.g., through-connection, interface, connector, coupling) formed from or including an exterior of a biocompatible and biostable material. The feedthrough 118 facilitates electric transmission through the base 112, from the interior of the base 112 to the exterior of the base 112 and vice versa.

By way of example, during use of the implantable medical device 110, a charge stored in a capacitor interior to the base 112 may be discharged in the form of an electrical pulse. The electrical pulse is transferred through a wall of the base 112 via the feedthrough 118. The electrical pulse is then received by at least one of the proximal ends 120 of the leads 114 and transmitted via conductive pathways through at least one of the leads 114 to electrodes 122, which may be located at distal ends of the leads 114. The electrodes 122 may be coupled to a heart 124 or other part(s) of the patient 116 to promote a pattern of heartbeats, stimulate heartbeats, sense heartbeats, promote healing, or for other reasons.

In some embodiments, activity is sensed via the electrodes 122 and communicated by the leads 114 to control circuitry in the base 112 via the feedthrough 118. The sensed activity may be used as feedback by the control circuitry to manage the operation of the device 110. In still other embodiments, the feedthrough 118 may also be used to facilitate transfer of electricity to the energy storage device within the base 112, such as for recharging or testing. In other embodiments, other energy storage devices may be used, such as a hybrid system using a combination of a battery and a capacitor for energy storage. According to an exemplary embodiment, two or more leads may be coupled to the interior of the base 112 via the feedthrough 118. In other embodiments, a single lead may be used (see generally device 210 as shown in FIG. 2).

Figure 2:
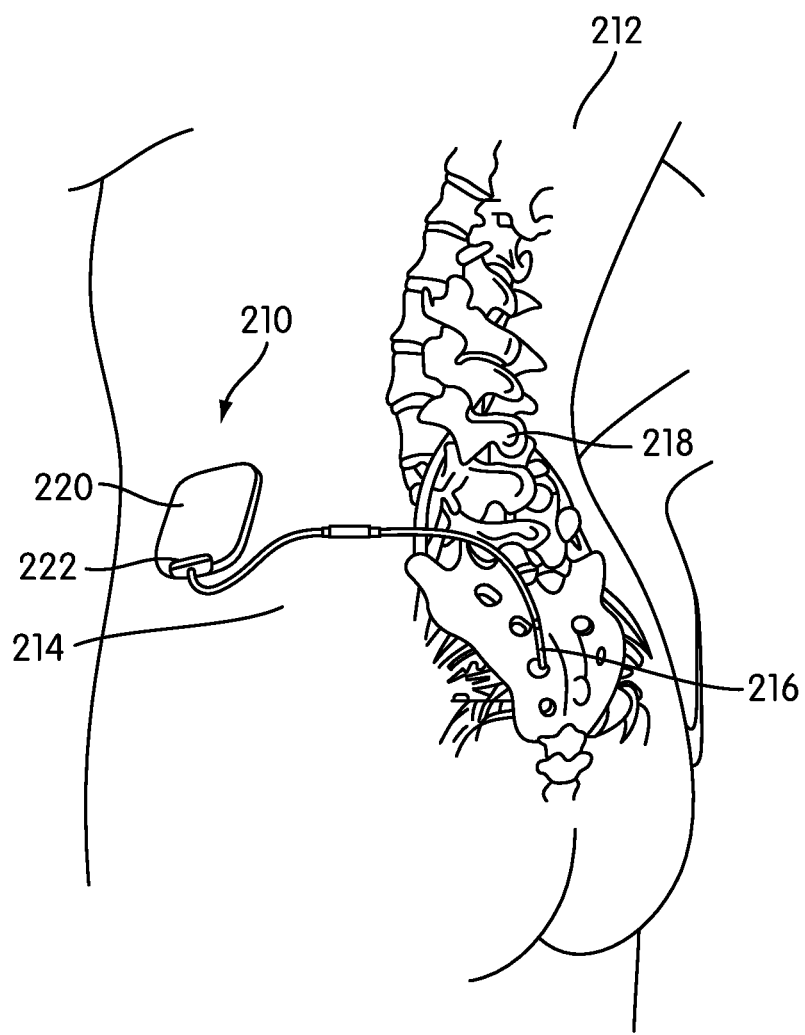
FIG. 2 is schematic view of another medical device implanted within a patient according to an exemplary embodiment.

Referring to FIG. 2, an implantable medical device 210 (e.g., electrical stimulator, neurostimulator) is configured to influence a nervous system and/or organs of a patient 212. The device 210 may be implanted, for example, into a subcutaneous pocket in an abdomen 214, pectoral region, upper buttocks, or other area of the patient 212, and the device 210 may be programmed to provide a stimulation signal (e.g., electrical pulse, frequency, voltage) associated with a specific therapy. During use, electrical contacts integrated with a lead 216 are placed at a desired stimulation site, such as a portion of a spine 218 or brain. The lead 216 is also connected to a base 220 of the device 210 by way of a feedthrough 222 integrated with an exterior surface of the base 220. In some contemplated embodiments, a feedthrough can transmit therapy and/or send signals directly to electrodes mounted on the implantable medical device (e.g., so-called leadless devices).

According to an exemplary embodiment, the feedthrough 222, as well as the rest the exterior of the base 220, is designed to be hermetically sealed, biocompatible, and biostable in order to prevent leakage of bodily fluids to the interior of the base 220, as well as to prevent leakage from the interior of the base 220 into the body during the usable life of the implantable medical device 210. According to an exemplary embodiment, the feedthrough 222 is hermetically sealed, and remains hermetically sealed when implanted in the body, displaying long-term biostability on the order of years, such as at least a year, five years, ten years, twenty years, or more.

Standard testing, such as in-vitro highly-accelerated immersion testing for hermeticity and dye infiltration, may be used to provide a reliable indicator of the ability of the feedthroughs 118, 222 to remain hermetically sealed and biostable when implanted over an extended period. Long-term hermeticity and/or biostability may be demonstrated by the occurrence of substantially no dye infiltration and substantially no loss of the hermetic seal (i.e., evidenced by the absence of dye penetration, helium leak, etc.) through the feedthrough after immersion in simulated body fluid at a controlled temperature (e.g., 120° C., 150° C., 200° C. or more) and pressure (e.g., 1.5 atm, 3.5 atm) over an extended test duration (e.g., 48 hours, 72 hours, 96 hours, a month or more), while maintaining high electrical conductivity through the feedthrough 222. Other standard tests, such as a Helium leak test and a 3-point bending strength test, may also evidence long-term biostability, as may be indicated by minimal degradation of strength and retention of low Helium leak rates, typically less than $1 \times 10^{-8}$ atm-cc He per second (e.g., less than $5 \times 10^{-9}$ atm-cc He per second).

Although described herein with respect to particular implantable medical devices, it should be understood that the concepts disclosed herein may be utilized in conjunction with a wide range of implantable medical devices, such as pacemakers, implantable cardioverter-defibrillators, sensors, cardiac contractility modulators, cardioverters, drug administering devices, diagnostic recorders, cochlear implants, and other devices. According to still other contemplated embodiments, devices other than implantable medical devices may also benefit from the concepts disclosed herein.

Figure 3:
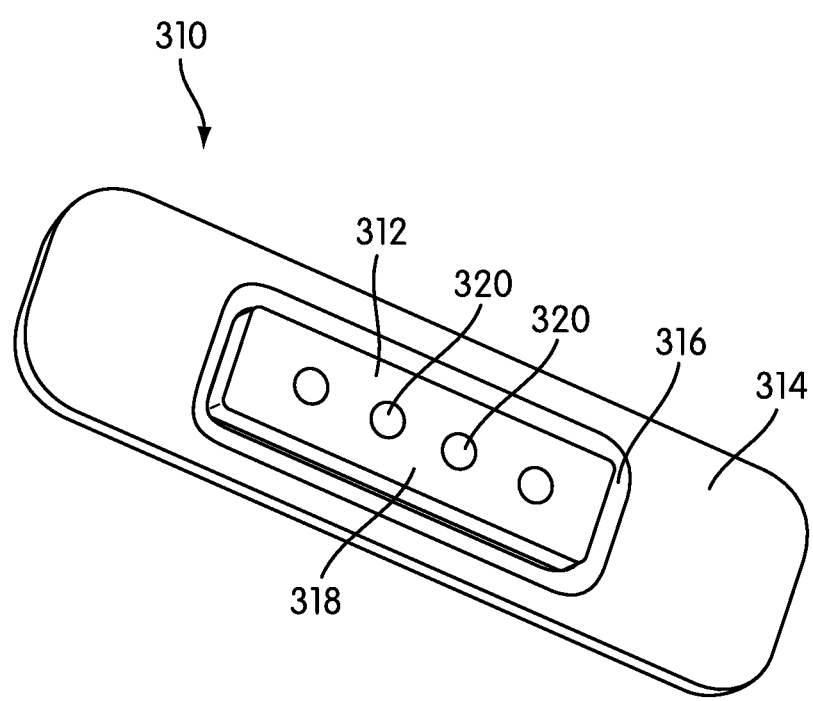
FIG. 3 is a perspective view of a portion of a medical device including a feedthrough according to an exemplary embodiment.

Referring now to FIG. 3, a wall 310 or encasement structure of an implantable medical device (see, e.g., implantable medical devices 110 and 210 as shown in FIGS. 1-2) includes a feedthrough 312. The feedthrough 312 is fastened to a portion 314 of the wall 310, such as a ferrule, in a recess 316 of the wall 310 that is configured to receive the feedthrough 312. The wall 310 may be integrated with another wall or walls to form a biocompatible, hermetically-sealed exterior for a base (see, e.g., bases 112 and 220 as shown in FIGS. 1-2) of the implantable medical device. In other embodiments, a ferrule does not include a recess. In still other embodiments, a feedthrough may be integrated directly into a wall, without use of a ferrule.

According to an exemplary embodiment, the feedthrough 312 is primarily formed from a material 318 that is generally electrically non-conductive, an insulator, or a dielectric. The feedthrough further includes one or more conduits 320 (e.g., conductive member, vertical interconnect access (via), path, pathway) that are generally electrically conductive and that extend through the material 318 of the feedthrough 312 that is generally electrically non-conductive. In some contemplated embodiments, the conduits 320 are integrated with the material 318 but do not extend through the material 318, and instead extend along a surface of the material 318, or on the surface of an intermediary material between the conduits 320 and the surface of the material 318. In this manner, the electrical signal can be conducted in a horizontal direction between conductive conduits (e.g., vias) or external pads, or otherwise connecting internal and/or external points that are laterally disposed from one another.

Figure 4:
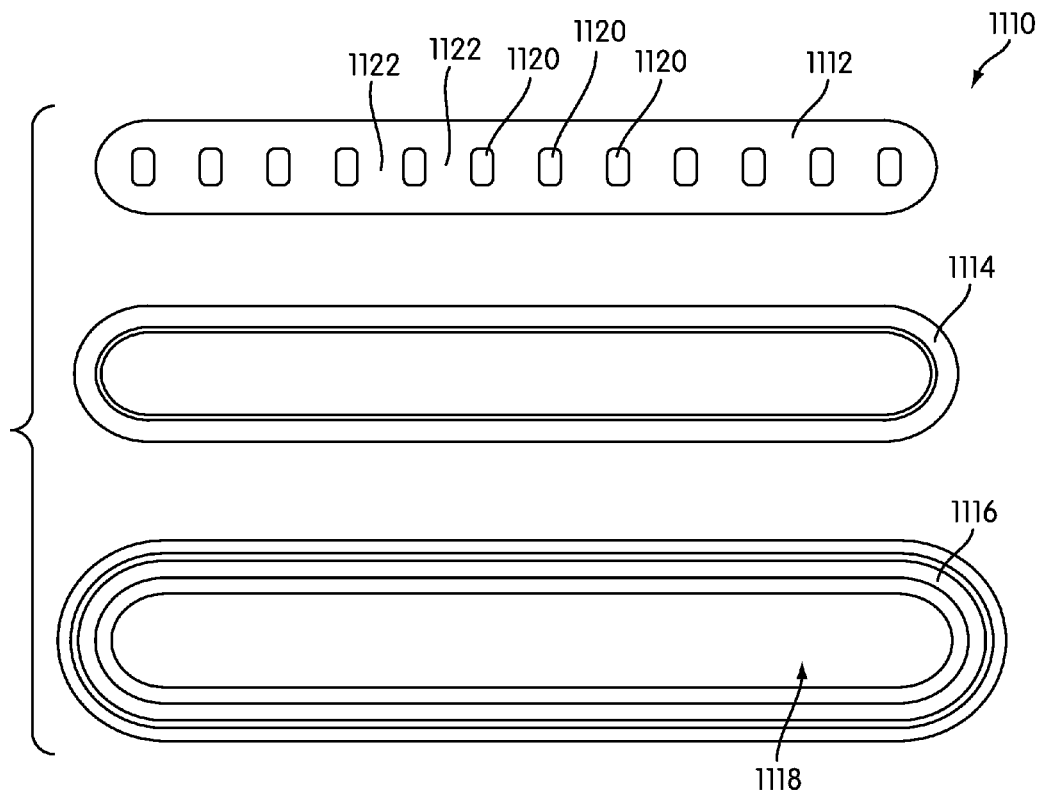
FIG. 4 is an exploded view of a portion of a medical device according to another exemplary embodiment.
Figure 5:
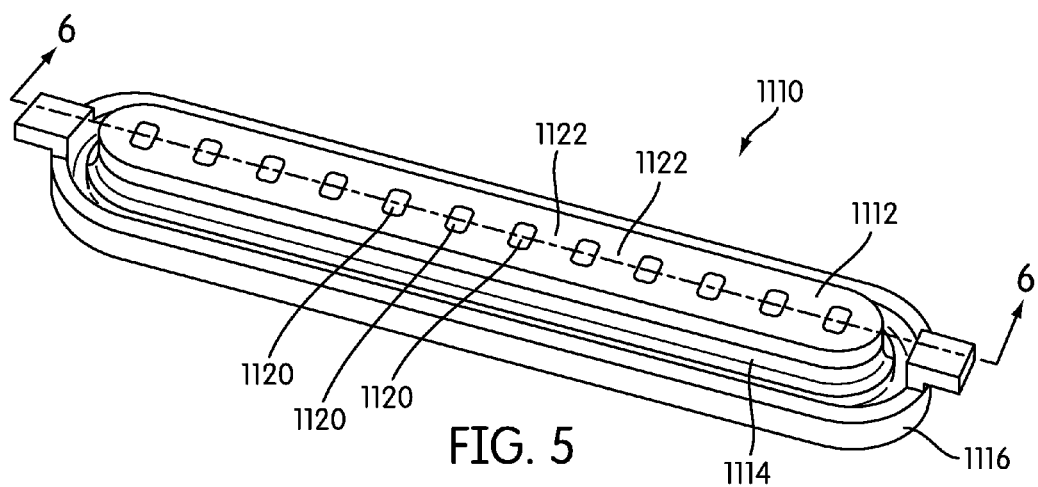
FIG. 5 is a perspective view of the portion of the medical device of FIG. 4.

Referring to FIGS. 4-5, components of an implantable medical device 1110 include a feedthrough 1112 (e.g., co-fired ceramic, monolith), a ring 1114 of filler material for brazing, and a ferrule 1116. During assembly of the implantable medical device 1110, the feedthrough 1112 is inserted into a recess 1118 (e.g., opening) in the ferrule 1116, the ring 1114 is then melted and brazed between the feedthrough 1112 and the ferrule 1116. In some embodiments, the ring 1114 is a gold ring, and the ferrule 1116 is formed from titanium. Gold and titanium are used in some embodiments due to the associated biocompatible properties and relative melting temperatures. In some embodiments, side walls of the ceramic insulator are coated (e.g., by a variety of potential methods, such as physical vapor deposition, sputtering, electron-beam evaporation, plating, chemical vapor deposition)

with a metal, such as niobium, titanium, molybdenum, or other biocompatible materials, to facilitate joining between the insulator and the ferrule. The coat of metal may facilitate adhesion and brazing of a pre-form gold ring to join the insulator and ferrule. In other contemplated embodiments, a ring and ferrule are formed from different materials or combinations of materials.

Figure 6:
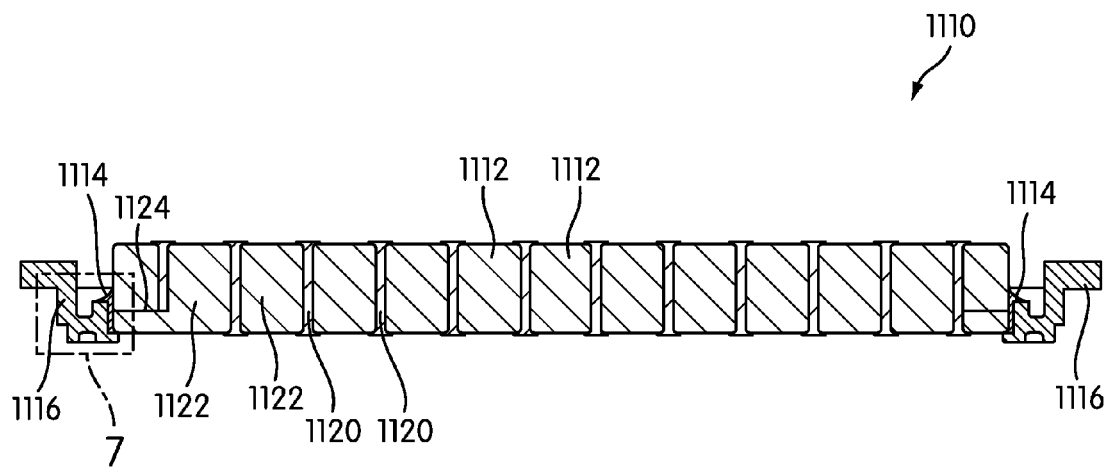
FIG. 6 is a sectional view of the portion of the medical device of FIG. 4, taken along line 6-6 as shown in FIG. 5.
Figure 7:
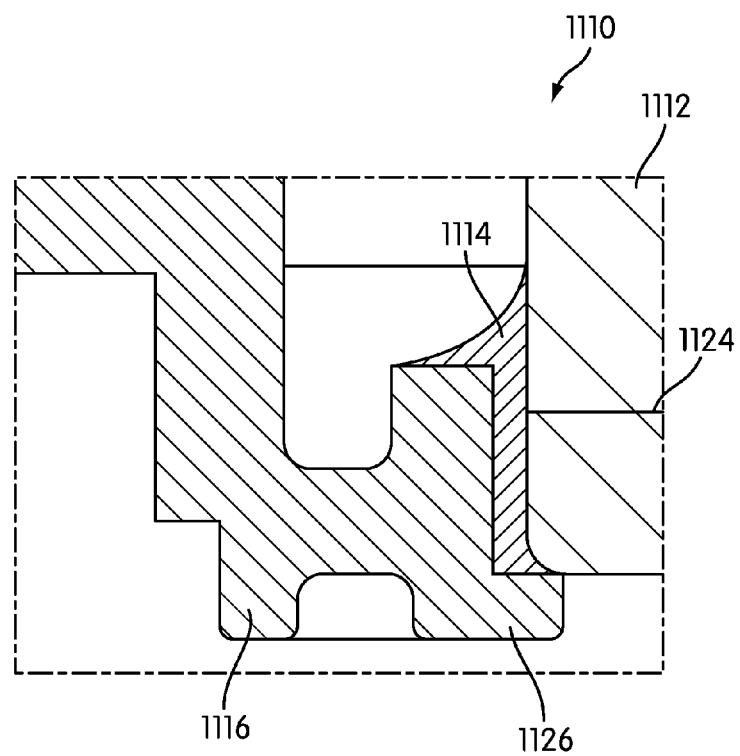
FIG. 7 is a sectional view of the portion of the medical device of FIG. 4, taken along area 7 as shown in FIG. 6.

Referring to FIGS. 6-7, the feedthrough 1112 includes conductive conduits 1120 (e.g., via) extending through an insulator 1122, between top and bottom surfaces of the feedthrough 1112. In some embodiments, at least one of the conductive conduits 1120 extends partially through the insulator 1122, and couples to a horizontal conduit 1124 (FIG. 7) that extends laterally to a side of the feedthrough 1112. In other embodiments, a conduit may extend fully through a feedthrough, such as from a top to a bottom and still connect horizontally to another body. In FIG. 7, the horizontal conduit 1124 extends to the ring 1114, brazed between the ferrule 1116 and feedthrough 1112. Accordingly, the horizontal conduit 1124 may serve as a ground plane for the feedthrough 1112. In some embodiments, the conductive conduits 1120, including the horizontal conduit 1124, include platinum. In some such embodiments, the horizontal conduit 1124 is printed onto a layer of un-fired (e.g., green) ceramic material, and co-fired with the other conductive conduits 1120 and insulator 1124.

Figure 8:
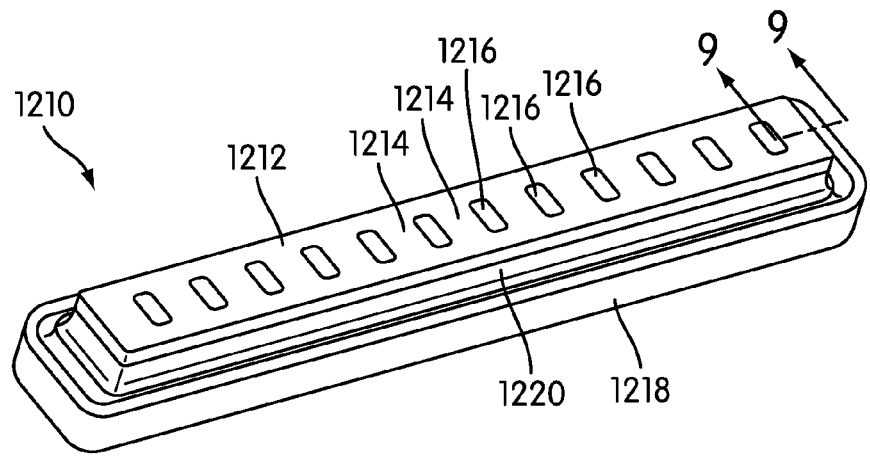
FIG. 8 is a perspective view of a portion of a medical device according to yet another exemplary embodiment.
Figure 9:
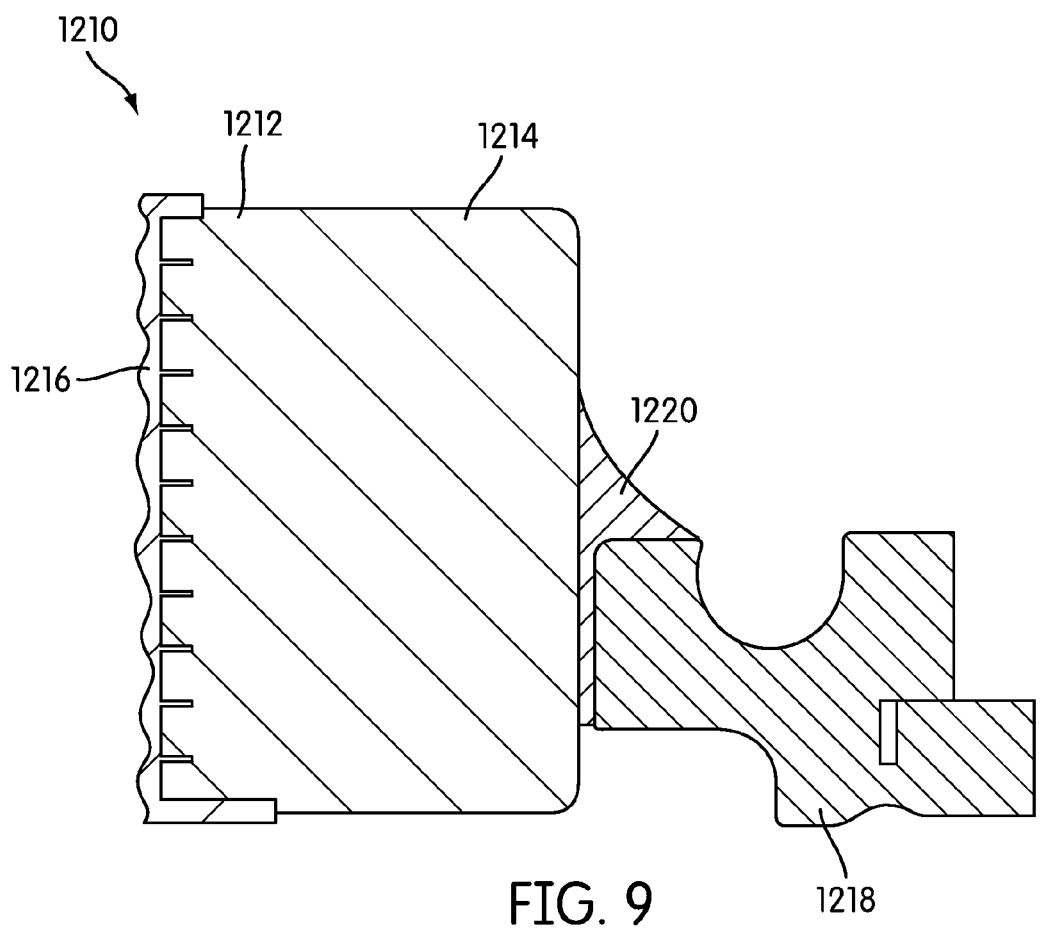
FIG. 9 is a sectional view of the portion of the medical device of FIG. 8, taken along line 9-9 as shown in FIG. 8.
Figure 10:
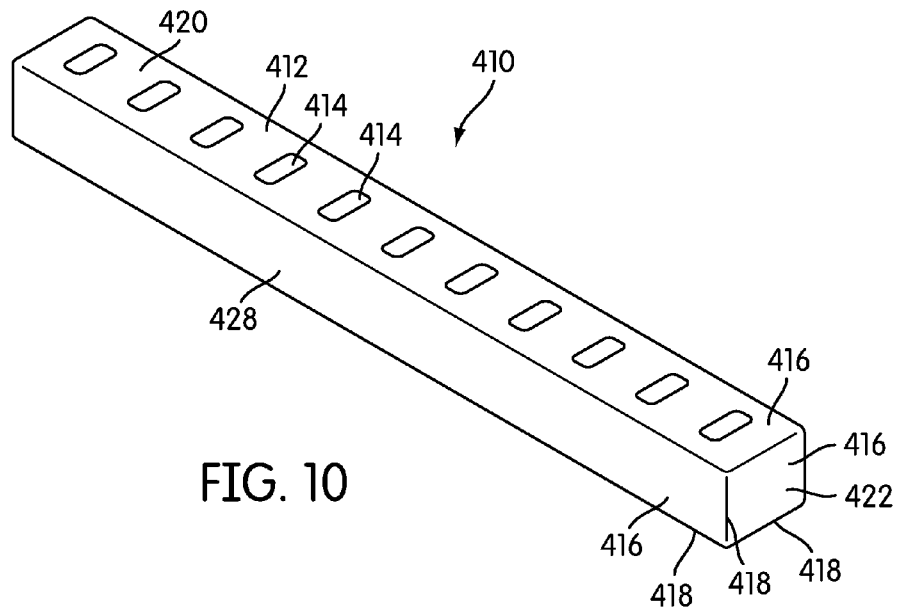
FIG. 10 is a perspective view of a feedthrough according to an exemplary embodiment.
Figure 11:
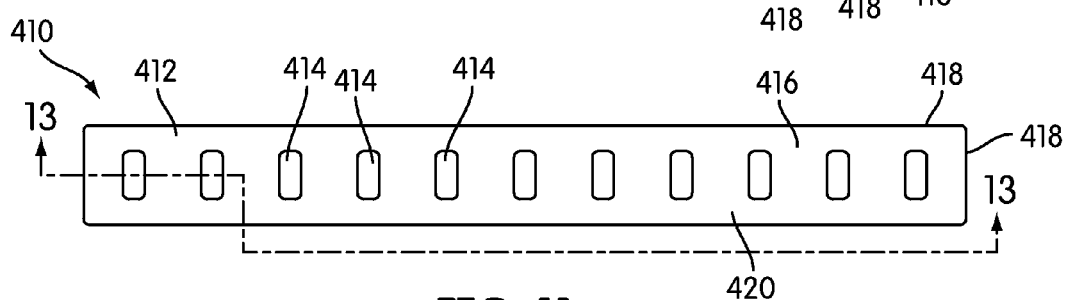
FIG. 11 is a top view of the feedthrough of FIG. 10.
Figure 12:
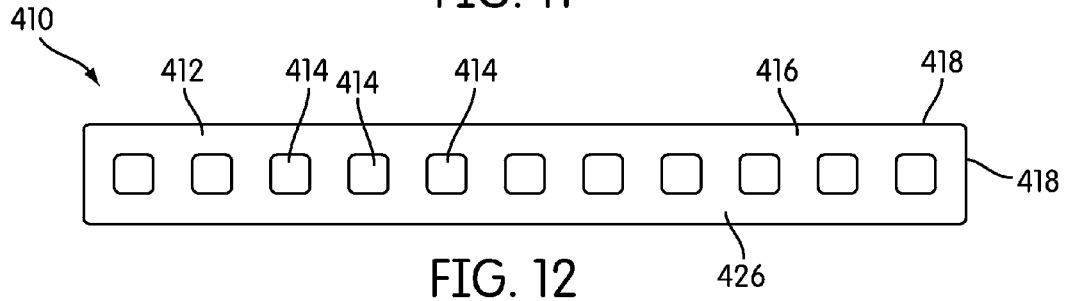
FIG. 12 is a bottom view of the feedthrough of FIG. 10.

Referring to FIGS. 8-9, a co-fired feedthrough 1212 includes a substantially rectangular insulator body 1214 with conductive conduits 1216. The feedthrough 1212 has been brazed into a ferrule 1218 of an implantable medical device 1210 with a ring 1220 of a biocompatible material. The prismatic shape of the rectangular insulator body 1214 (FIG. 8) is believed to improve the braze joint stability, as discussed in more detail below. According to an exemplary embodiment, the ferrule 1218 is ledge-less, where the insulator body is not supported by a flange or extension on the underside of the ferrule 1218, as compared to the ferrule 1116 having a ledge 1126 as shown in FIG. 7. The ledge-less design of the ferrule 1218 is intended to improve electrical isolation of the conductive conduits 1216 of the feedthrough 1212, by increasing the path length for shorting between the conductive conduits 1216 and the ferrule 1218, which is further intended to improve external interconnect access (e.g., a lead coupled to the feedthrough 1212).

Referring now to FIGS. 10-13, a feedthrough 410 is shown according to another exemplary embodiment and includes a body 412 (e.g., insulator) and at least one conduit 414 (e.g., conductive pathway, electrical conduit, via). As shown, the feedthrough 410 includes eleven conduits 414, but according to other embodiments may include a greater or lesser number of conduits, or different layout of conduits. According to an exemplary embodiment, the body 412 is formed from a material that is an electrical insulator, and in some embodiments the body 412 includes substantially flat faces 416 (e.g., sides, exterior surfaces). The faces 416 are separated from one another by corners 418 or edges.

According to an exemplary embodiment, the feedthrough 410 further includes the conduit(s) 414 configured to conduct electricity through the electrical insulator material of the body 412. The conduit 414 may be substantially straight or tortuous (e.g., staggered, serpentine, zigzag). A tortuous path for the conduit 414 may improve the hermetic seal of the feedthrough 410 by better impeding fluid from seeping (e.g., passing, ingress) between the conduit 414 and the body 412. However, a tortuous path may increase electrical resistance, decreasing efficiency of the feedthrough 410 relative to a conduit with a substantially straight path (e.g., overlaying a straight line). In some embodiments, resistance of the metallization is less than about 30 mΩ, such as less than about 10 mΩ. In other embodiments, the resistance of the metallization is less than about 100 mΩ. The resistance of the metallization may vary as a function of the diameter of the conduit 414, the thickness of the body 412, materials, and other properties. In some designs, resistance is increased as a conduit is staggered or made tortuous in order to bolster hermeticity, however it has been found that a tortuous path, and the associated resistance losses, may be unnecessary given the proper combination of materials, design, and co-firing processes.

In some embodiments, the faces 416 and corners 418 of the body 412 together form a substantially prismatic or rectilinear exterior form factor for the feedthrough 410 in which at least some faces 416 of the body 412 (e.g., top 420 relative to end 422) are substantially orthogonal to one another or substantially parallel with one another. In some such embodiments, all of the faces 416 of the body 412 are either substantially orthogonal or substantially parallel to one another. In other embodiments, none of the faces are substantially orthogonal to one another. In still other embodiments, at least some faces are not flat.

According to an exemplary embodiment, the feedthrough 410 is provided in the form of a box-like structure with rectangular faces 416, such as a block, a brick, or a cube. In some such embodiments, the body 412 includes the top 420, a bottom 426, and sides (e.g., ends 422 and lengthwise sides 428) extending between the top 420 and bottom 426. Each of the sides 422, 428 includes a flat surface. In some embodiments, the flat surfaces of the ends 422 are substantially the same size and shape as one another, and the flat surfaces of the lengthwise sides are substantially the same size and shape as one another. In other contemplated embodiments, a feedthrough is generally cylindrical, oval, or otherwise shaped.

Still referring to FIGS. 10-13, the flat surfaces of the ends 422 of the body 412 are parallel to one another. In some such embodiments, the top 420 and bottom 426 of the body 412 include flat surfaces orthogonal to the flat surfaces of the ends 422 of the body 412. In some such embodiments, the sides 428 extending lengthwise along the body 412 include flat surfaces that are also orthogonal to the flat surfaces of the ends 422 of the body 412. According to such an embodiment, three cross-sections of the body 412 that are orthogonal to one another, each have substantially rectangular peripheries. For example, one rectangular cross-section extends in a lengthwise direction, another extends across the width of the body, and a third rectangular cross-section cuts the body along a horizontal plane.

According to an exemplary embodiment, the body 412 of the feedthrough 410 further includes the corners 418 between the faces 416 of the exterior of the feedthrough 410. The corners 418 and edges may be right-angle corners, or may be otherwise angled. In some embodiments, the corners 418 are rounded (e.g., radiused, smoothed, dulled). According to an exemplary embodiment, the corners 418 are rounded by tumbling, grinding, milling, polishing, or another shaping process after the body 412 is cut into a rectilinear shape. In such embodiments, the corners 418 are gradually worn by an abrasive agent, such as silicon carbide grit. Controlled and limited application of the shaping process may sufficiently maintain a relatively precise geometry of the body 412, while reducing the potential for stress concentrations and crack initiation sites provided by the corners 418. Controlled and limited shaping may also reduce the potential for damage to occur below the surface of the insulator body 412. However, in still other contemplated embodiments, the corners may be beveled or sharp.

According to an exemplary embodiment, the body 412 of the feedthrough 410 is formed from a ceramic material, and the conduit 414 is formed from a metallic paste (e.g., via paste). During manufacturing of the feedthrough 410, the metallic paste of the conduit 414 is filled into a hole 424 (e.g., square hole, round hole, oval hole, etc.) in the ceramic material of the body 412 (see generally FIG. 21 discussed below). The body 412 and conduit 414 of the feedthrough 410 are then co-fired—both the ceramic material of the body 412 and the metallic paste of the conduit 414 are fired together in a kiln at the same time, such as at a temperature of about 1600° C. for about an hour.

According to an exemplary embodiment, the material of the body 412 includes alumina (e.g., aluminum oxide, corundum), such as at least 70% alumina or about 92% or 96% alumina. In some embodiments, the metallic paste of the conduit 414 primarily includes platinum (e.g., platinum powder) and an additive, where the additive comprises alumina (e.g., $d_{50}$ of 1-10 μm alumina powder). The metallic paste may include a first platinum powder having a median particle size between 3 to 10 μm (e.g., $d_{50}$ median particle size), a second, coarser platinum powder having a median particle size between 5 to 20 μm, or a combination of platinum powders. In other contemplated embodiments, such as those that may or may not be intended for use in an implant, the paste may include titanium, niobium, zirconium, tantalum, other refractory metals, alloys thereof, oxides thereof, or other materials.

Use of different size particles for the materials of the metallic paste, including additives, is believed to change the thermal expansion response and/or sintering kinetics and properties (e.g., sintering shrinkage, shrinking profile) of the metallic paste, which may be adjusted as necessary to be compatible with the other materials of the co-fired feedthrough, such as the material of the body 412. Furthermore in some embodiments, during the co-firing process, alumina of the body 412 is sintered, and the alumina that is an additive of the metallic paste may improve adhesion between the metallic paste of the conduit 414 and the alumina of the body 412 forming a strong co-fired bond therebetween.

Figure 14:
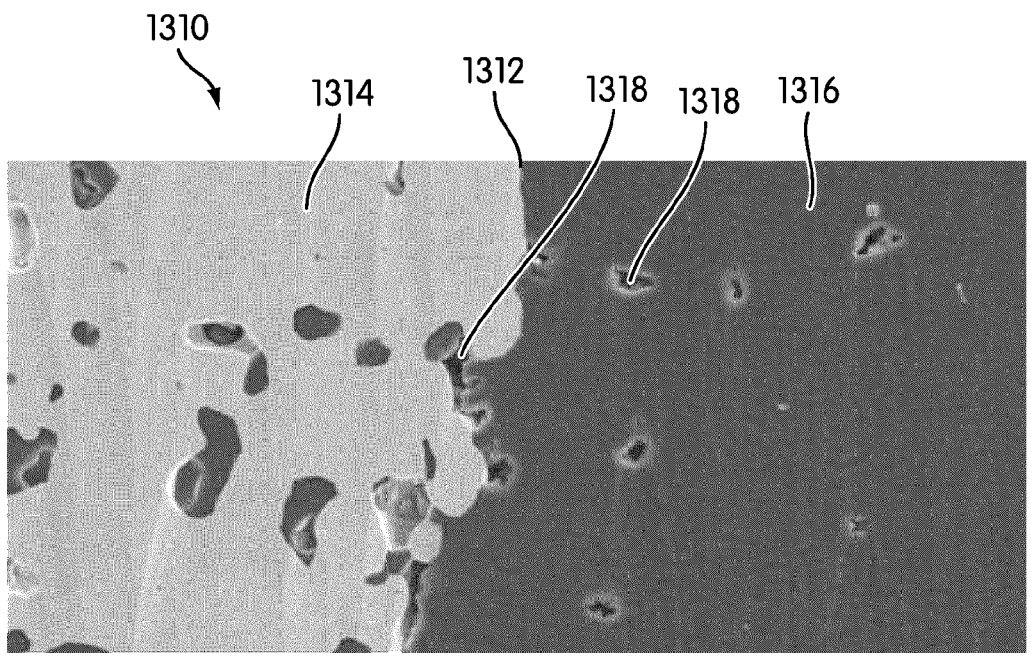
FIG. 14 is a sectional scanning electron microscopy (SEM) micrograph of an interface between a conductive conduit and a insulator according to an exemplary embodiment.
Figure 15:
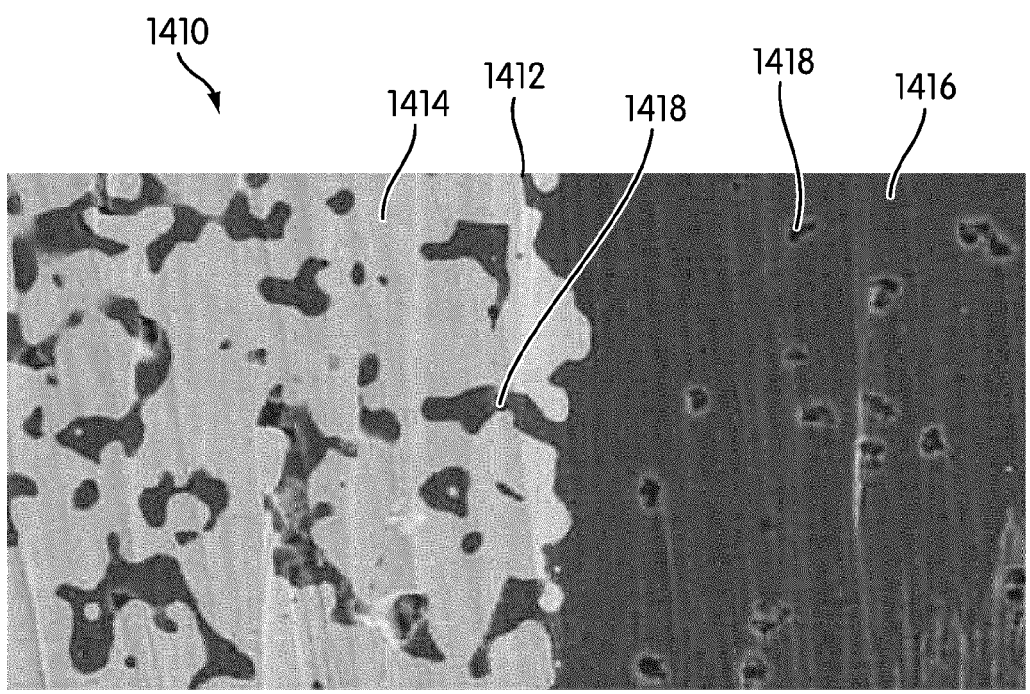
FIG. 15 is a sectional SEM micrograph of an interface between a conductive conduit and a insulator according to another exemplary embodiment.

On a micro-scale, the alumina in the metallic paste may bond with the alumina of the body 412 along the border (e.g., boundary, interface) between the conduit 414 and the body 412 in the hole 424 (see generally scanning electron microscopy as shown in FIGS. 14-15). The bond formed with the alumina as an additive in the metallic paste is believed to significantly improve the hermetic seal, when compared to the bond between the conduit 414 and the body 412 without alumina as an additive in the metallic paste, because of the interaction between the alumina additive and alumina of the body 412. Inclusion of alumina as an additive in the metallic paste may reduce the size and quantity of voids, and may also improve the thermal expansion compatibility of the metallic paste with the ceramic of the body 412 during the co-firing process, reducing stresses otherwise caused by unequal expansions or contraction of the different materials of the feedthrough 410 and forming a hermetic, biostable co-fired bond.

Due at least in part to the combination of materials selected for the body 412 and conduit 414, the result of the co-firing process is that the conduit 414 is hermetically sealed with the body 412. Fluids, such as bodily liquids and gases, are prevented from passing through the conduit 414 or between the conduit 414 and the body 412 of the feedthrough 410, such as through a chain of micro-pores at the interface. Furthermore, the feedthrough 410 remains biostable, with the hermetic seal not breaking down over a long duration, on the order of years.

Referring to FIGS. 14-15, co-fired feedthroughs 1310, 1410 include interfaces 1312, 1412 between materials of conductive conduits 1314, 1414 and insulator bodies 1316, 1416 that differ from one another at least in part due to additives used in the materials of the conductive conduits 1314, 1414. While the material of the insulator bodies 1316, 1416 shown in FIGS. 14-15 is substantially the same (e.g., about 92% alumina), the materials of the conductive conduit 1314, shown in FIG. 14, includes platinum (e.g., platinum powder in the form of a paste for co-firing) with additives of $Al_2O_3$, $SiO_2$, CaO, MgO, while the material of the conductive conduit 1414, shown in FIG. 15, includes platinum with only $Al_2O_3$ as an additive. The co-fired interfaces 1312, 1412 of FIGS. 14-15 both include some initial defects 1318, 1418 (e.g., voids, pores). However, it has been found that use of only $Al_2O_3$ as an additive decreases the quantity and/or magnitude of the initial defects 1418, providing an improved interface 1412 (e.g., co-fired bond).

For purposes of context and as summarized in TABLE 1, a set of via metallization compositions was evaluated for parameters relevant to co-firing and feedthrough performance, such as via projections, adhesion, warpage, resistivity, and hermeticity. Different additives and combinations of additives (e.g., $Al_2O_3$ alone; $Al_2O_3$, $SiO_2$, MgO, and CaO; and $SiO_2$, MgO, and CaO) were provided to a paste of platinum at different levels of concentration, ranging from 0-10% of the paste.

TABLE 1

| Designation | Additives | Level Related to Additive Concentration (between 0-10%) | | | |
| --- | --- | --- | --- | --- | --- |
| | | Level 0 | Level 1 | Level 2 | Level 3 |
| A | $Al_2O_3$ alone | | A1 | A2 | A3 |
| B | $Al_2O_3$, $SiO_2$, MgO, and CaO | P | B1 | B2 | B3 |
| C | $SiO_2$, MgO, and CaO | | C1 | C2 | C3 |

In the evaluation corresponding to TABLE 1, provided for context, hermeticity was evaluated using a He leak test before and after thermal shock testing, which included 5 and 500 cycles ranging from −50° C. to 165° C. As shown in TABLE 2, the formulation corresponding to B2 remained hermetically sealed according to the He leak test, even after 500 cycles.

TABLE 2

| Composition | Insulator | Initial He Leak | after 5 cycles | after 500 cycles |
| --- | --- | --- | --- | --- |
| Pt + 5% ($Al_2O_3$, $SiO_2$, MgO, and CaO) | Alumina | 20 of 20 no leak | 20 of 20 no leak | 20 of 20 no leak |

For purposes of further context, a series of feedthrough parts (designated TS4.6, TS4.8 and TS 5) were manufactured using the formulation of TABLE 2. As summarized in TABLE 3, it was noted that, while the conductive conduits (e.g., vias) were initially hermetic, having passed the He leak tests, a significant fraction of conductive conduits (e.g., up to 3%) was found to exhibit dye penetration down some length of the via.

TABLE 3

|  | Diameter (mil) | Length (mil) | Pitch (mm) | Path | He Leak | Pieces | Via | | Dye Penetration (via) |
|---|---|---|---|---|---|---|---|---|---|
| TS4.6 | 6 | 42 | 0.51 | straight | pass | 10 | 200 | 4 | 2.0% |
|  | 6 | 42 | 0.79 | straight | pass | 10 | 130 | 4 | 3.1% |
|  | 6 | 42 | 0.46 | straight | pass | 10 | 200 | 1 | 0.5% |
|  | 6 | 42 | 0.56 | straight | pass | 10 | 260 | 3 | 1.2% |
| TS4.6 | 6 | 66 | 0.51 | straight | pass | 10 | 200 | 5 | 2.5% |
|  | 6 | 66 | 0.79 | straight | pass | 10 | 130 | 2 | 1.5% |
|  | 6 | 66 | 0.51 | straight | pass | 10 | 200 | 5 | 2.5% |
|  | 6 | 66 | 0.56 | straight | pass | 10 | 260 | 4 | 1.5% |
| TS4.8 | 8 | 66 | 0.64 | straight | pass | 10 | 170 | 5 | 2.9% |
|  | 8 | 66 | 1.02 | straight | pass | 10 | 110 | 3 | 2.7% |
|  | 8 | 66 | 0.51 | straight | pass | 10 | 200 | 3 | 1.5% |
|  | 8 | 66 | 0.64 | straight | pass | 10 | 200 | 6 | 3.0% |
|  | 8 | 66 | 0.81 | staggered | pass | 10 | 320 | 1 | 0.3% |
| TS5 | 8 | 42 | min. 0.71 | straight | pass | 10 | 280 | 0 | 0 |

In TABLE 3, the "diameter," "length," and "pitch" columns correspond to characteristics of the conductive conduits (i.e., via); the "path" column indicates whether the conductive conduits were stacked to form a straight or staggered path; the "He Leak" column indicates whether the configuration passed a He leak test; the "Pieces" and "Via" column provide the number of via tested as well as the number of corresponding pieces in which the via were located; and the "Dye Penetration" column indicates the number of via exhibiting dye penetration and the percentage of total via tested. Following the successful performance in thermal shock tests, evidence of dye penetration was unexpected. To address this unexpected result of dye penetration shown in TABLE 3, a number of factors potentially affecting via hermeticity were evaluated, including design and process conditions, in addition to inorganic and organic components in the via paste. Of these, the inorganic additives were found to strongly influence the hermeticity of the resulting co-fired structure.

As summarized in the following table, provided for purposes of example, the percentage of alumina additive to paste of platinum powder having a particle size distribution $d_{50}$ in the range of 3-10 μm ("Pt-1") influenced the resistance of the conductive conduit (e.g., metallization resistance of the via):

thermo-mechanical analysis; the "Penetrated" row includes the number of samples that exhibited dye penetration; the "He Leak" row includes the number of samples that exhibited Helium leakage during testing; the "Metallization Resistivity" row includes the bulk electrical resistivity of the metallization; the "Via Resistance" row includes the electrical resistance of the conductive conduit, with other influencing factors, such as thickness (e.g., 66 mill) and diameter of the conduit held substantially constant; and the "Adhesion Failure Location" row details the location of failure in a standard soldered pin-pull test. While none of the 700 the samples with 2.5% alumina additive showed dye penetration, the samples with 5% alumina additive exhibited better performance. As shown in the examples of TABLE 4, it has been generally found that with the inclusion of alumina as an additive, and in the absence of "Other" additives, such as $SiO_2$, MgO, and CaO, the adhesion improved and electrical resistance decreased, but at a cost of increased height of via projections and increased sample warpage.

To mitigate the projection and warpage of the co-fired conductive conduit (i.e., via), the use of different particle

TABLE 4

| Alumina | 2.5% | 3% | 3.5% | 4% | 4.5% | 5% |
|---|---|---|---|---|---|---|
| Other | 2.5% | 0 | 0 | 0 | 0 | 0 |
| Via Projection | <10 μm | >20 μm | >20 μm | >20 μm | >20 μm | >20 μm |
| Warpage | <5 μm | >50 μm | >50 μm | >50 μm | >50 μm | >50 μm |
| Shrinkage | 15% | 10% | 10% | 10% | 10% | 10% |
| Penetrated | 0 of 700 | 0 of 700 | 0 of 700 | 0 of 700 | 0 of 700 | 0 of 700 |
| He Leak | 0 of 700 | 0 of 700 | 0 of 700 | 0 of 700 | 0 of 700 | 0 of 700 |
| Metallization Resistivity (line) | $28.5 \times 10^{-8}$ Ω·m | $15.1 \times 10^{-8}$ Ω·m | $16.4 \times 10^{-8}$ Ω·m | $17.7 \times 10^{-8}$ Ω·m | $19.0 \times 10^{-8}$ Ω·m | $20.3 \times 10^{-8}$ Ω·m |
| Via Resistance | 7.8 mΩ | 6.8 mΩ | 6.9 mΩ | 6.7 mΩ | 6.2 mΩ | 6.6 mΩ |
| Adhesion Failure Location | alumina | alumina | alumina | alumina | alumina | alumina | where the "Alumina" row includes the percentage of metallization paste that is alumina; the "Other" row includes the percentage of the metallization paste that is alumina as well as other additives $SiO_2$, MgO, and CaO; the "Projection" row includes the height of the projection of the via metallization; the "Warpage" row includes the magnitudes of the relative warpage of the substrate (e.g., insulator); the "Shrinkage" row includes the shrinkage of the metallization determined by sizes of the platinum powder for the metallization paste used to construct the conductive conduits were screened. In some exemplary formulations, a coarser platinum powder, having an average particle size distribution $d_{50}$ in the range of 5-20 μm ("Pt-2"), and/or mixed the Pt-2 powder with the Pt-1 powder, was used, as summarized by the following table provided for context.

TABLE 5

| Pt-1:Pt-2 | 1:0 | 0:1 | 1:0 | 1:0 | 9:1 | 4:1 |
|---|---|---|---|---|---|---|
| Alumina | 2.5% | 0 | 4% | 5% | 4% | 4% |
| Other | 2.5% | 0 | 0 | 0 | 0 | 0 |
| Via Projection | <10 μm | | >20 μm | >20 μm | >20 μm | >20 μm |
| Warpage | <5 μm | 6 μm | >50 μm | >50 μm | 43 μm | 37 μm |
| Shrinkage | 15% | 10% | 10% | 10% | 10% | 11% |
| Penetrated | 0 of 700 | | 0 of 700 | 0 of 700 | 0 of 700 | 0 of 700 |
| He Leak | 0 of 700 | | 0 of 700 | 0 of 700 | 0 of 700 | 0 of 700 |
| Metallization Resistivity (line) | $28.5 \times 10^{-8}$ $\Omega \cdot m$ | $20.7 \times 10^{-8}$ $\Omega \cdot m$ | $17.7 \times 10^{-8}$ $\Omega \cdot m$ | $20.3 \times 10^{-8}$ $\Omega \cdot m$ | $18.7 \times 10^{-8}$ $\Omega \cdot m$ | $19.3 \times 10^{-8}$ $\Omega \cdot m$ |
| Via Resistance | 7.8 mΩ | | 6.7 mΩ | 6.6 mΩ | 6.6 mΩ | 6.8 mΩ |
| Adhesion Failure Location | alumina | alumina | alumina | alumina | alumina | alumina |

In TABLE 5, the "Pt-1:Pt-2" row includes the ratio of the two different size platinum powders used in the metallization paste, and the other rows match those of TABLE 4. Mixing of the two platinum powders in ratios of 9:1 and 4:1 decreased the relative projection and warpage of the co-fired conductive conduit from the insulator, but further decrease was preferred in some embodiments. The mixtures of Pt-1 and Pt-2 in combination with alumina additive were refined as summarized the following table provided for context:

TABLE 6

| Pt-1:Pt-2 | 7:3 | 7:3 | 7:3 | 1:1 | 1:1 | 1:1 |
|---|---|---|---|---|---|---|
| Alumina | 5% | 7% | 9% | 5% | 7% | 9% |
| Other | 0 | 0 | 0 | 0 | 0 | 0 |
| Via Projection | 15 μm | 15 μm | 20 μm | 10 μm | 10 μm | 15 μm |
| Warpage | 10 μm | 10 μm | 10 μm | <5 μm | <5 μm | <5 μm |
| Shrinkage | 13% | 12% | 11% | 15% | 13% | 12% |
| Penetrated | 0 of 700 | 0 of 700 | 0 of 700 | 0 of 700 | 0 of 700 | 0 of 700 |
| He Leak | 0 of 700 | 0 of 700 | 0 of 700 | 0 of 700 | 0 of 700 | 0 of 700 |
| Metallization Resistivity (line) | $20 \times 10^{-8}$ $\Omega \cdot m$ | $23 \times 10^{-8}$ $\Omega \cdot m$ | $27 \times 10^{-8}$ $\Omega \cdot m$ | $21 \times 10^{-8}$ $\Omega \cdot m$ | $24 \times 10^{-8}$ $\Omega \cdot m$ | $29 \times 10^{-8}$ $\Omega \cdot m$ |
| Via Resistance | 7.7 mΩ | 8.1 mΩ | 10.2 mΩ | 7.8 mΩ | 9.2 mΩ | 11.5 mΩ |
| Adhesion Failure Location | alumina | alumina | alumina | alumina | alumina | alumina |

The mixing of different size platinum powders and alumina additives resulted in formulations for via paste with decreased projections, matched shrinkage (reduced warpage) as well as controlled resistance of the metallization.

For purposes of context, a formulation of platinum paste comprising equal parts Pt-1 and Pt-2 platinum powders with 5% alumina additive was used in the production of a number of substantially rectangular top and bottom pad constructions for feedthroughs, as summarized in the following TABLE 7:

TABLE 7

| | Top Pad Pitch (mm) | | Top Pad Size (mm) | | Bottom Pad Size (mm) | | Thickness (mm) | Dye Penetration |
|---|---|---|---|---|---|---|---|---|
| | x | y | x | y | x | y | | |
| 1 | 14.008 | 40.611 | 0.450 | 0.953 | 0.784 | 0.784 | 1.660 | 0 of 108 |
| 2 | 14.015 | 40.610 | 0.445 | 0.948 | 0.785 | 0.790 | 1.656 | 0 of 108 |
| 3 | 14.016 | 40.603 | 0.444 | 0.944 | 0.781 | 0.793 | 1.659 | 0 of 108 |
| 4 | 14.013 | 40.615 | 0.453 | 0.942 | 0.788 | 0.792 | 1.660 | 0 of 108 |
| 5 | 14.028 | 40.647 | 0.456 | 0.950 | 0.784 | 0.787 | 1.659 | 0 of 108 |
| 6 | 14.010 | 40.603 | 0.455 | 0.948 | 0.789 | 0.793 | 1.661 | 0 of 108 |
| 7 | 14.018 | 40.596 | 0.455 | 0.950 | 0.790 | 0.794 | 1.661 | 0 of 108 |
| 8 | 14.007 | 40.628 | 0.447 | 0.952 | 0.786 | 0.789 | 1.666 | 0 of 108 |

The following TABLE 8 shows the results from biostability testing at 150° C. in de-ionized water for 5 days, and subsequent thermal shock tests:

TABLE 8

| Type of Test | Quantity Tested | Test Parameters | Dye Penetration |
|---|---|---|---|
| Immersion Testing | 15 pieces (105 via) | 150° C. in de-ionized water for 5 days | 0 of 15 pieces (0 of 105 via) |
| Thermal Shock | 15 pieces (105 via) | −65° C. to 150° C. for 1000 cycles | 0 of 15 pieces (0 of 105 via) |

The samples remained hermetic without any dye penetration.

Referring back to FIGS. 10-13, the body 412 is formed from a material, such as alumina, that may be difficult to cut or shape due to the hardness of the material when fired. With such embodiments, a rectilinear shape for the faces 416 the body 412 may be less difficult to form than a rounded shape. But, until recent discovery, a rectilinear shape was thought to promote structural weaknesses in a feedthrough and adjoining surfaces, such as due to increased stress concentrations and susceptibility to cracking caused by sharp corners of the feedthrough. Accordingly, prior hermetic feedthroughs included rounded ends (e.g., radiused ends, ovalized ends), which were time-consuming to form via grinding processes or post-firing machining However, a feedthrough 410 having ends 422 of the body 412 with flat surfaces has been discovered to improve the performance of the hermetic seal of the feedthrough 410 when integrated with or within a wall of an implantable medical device (see, e.g., FIG. 3), such as when metalized and brazed into a ferrule incorporated into an implantable medical device, without significant occurrence of the previously-feared drawbacks of a rectilinear shape. It was surprising to find during in-vitro, accelerated aging testing that durability significantly increased for the prismatic parts (e.g., flat ends), when compared to parts with radiused ends. Use of a body 412 with flat ends 422 is thought to improve the hermetic seal when the body 412 is integrated with the ferrule. The flatness of the ends 422 is believed due at least in part to the precision of the wafering saw with diamond cutting blades (or like instrument) used to cut of the material of the body 412, when compared to a less-precise grinding process used to round ends of prior feedthroughs. Additionally, the formation of flat, precisely cut ends 422 is thought to reduce the likelihood of defects, pores, or voids on the exterior surfaces of the body 412, which may provide a leak path for fluids.

By way of example, 50 rectangular bricks of insulator material were cut using a wafering saw with target dimensions of 6.426 mm in length and 1.778 mm in width. The average length of the 50 bricks was 6.437 mm with a standard deviation of 0.004 mm and the average width was 1.794 mm with a standard deviation of 0.004 mm. By contrast, in another set of 120 samples with rounded ends formed from cutting with a wafering saw followed by grinding, the average length of 6.455 mm, which varied by a standard deviation of 0.011 mm. Subsequently, after polishing 100 of the samples, the samples had an average length of 6.449 mm, which varied by a standard deviation of 0.010 mm. In width, the 120 samples with rounded ends had an average width of 1.808 mm with a standard deviation of 0.007 mm after grinding. Then after polishing, the 100 samples had an average width of 1.795 mm with a standard deviation of 0.009 mm. As such, the use of flat ends improved the dimensional accuracy of the insulator, while removing the additional manufacturing steps of grinding and polishing.

The relative immersion performance of the cofired brick shape (flat sides with flat ends; see, e.g., FIGS. 8 and 10-13) to the cofired radiused shape (flat sides with rounded ends; see, e.g., FIGS. 4-5) was assessed via testing by immersing gold-brazed insulators (e.g., gold-brazed ceramic, mostly alumina) into phosphate buffered saline (PBS) solution at 150° C. for up to 5 days. The same ferrule type/shape, gold preform, and brazing profile were used to braze the insulators in gold. Following the immersion period, the insulators were vacuum baked and the helium leak rate for each insulators was measured. The pushout strength of the gold braze joint was also measured. Results of the testing found that the radiused insulator shape lost up to 55% of its original pushout strength within 1.5 days at 150° C. in PBS solution, and about one-third of the radiused insulators leaked at rates faster than $5.0 \times 10^{-9}$ atm*cc He/sec. In comparison, the brick insulator shape showed no reduction in pushout strength after 5 days at 150° C. in PBS solution, with all parts remaining hermetic to better than $1.0 \times 10^{-10}$ atm*ccHe/sec. Accordingly, the testing indicated that the brick-shaped insulators had superior immersion performance compared to the radiused insulators.

Figure 21:
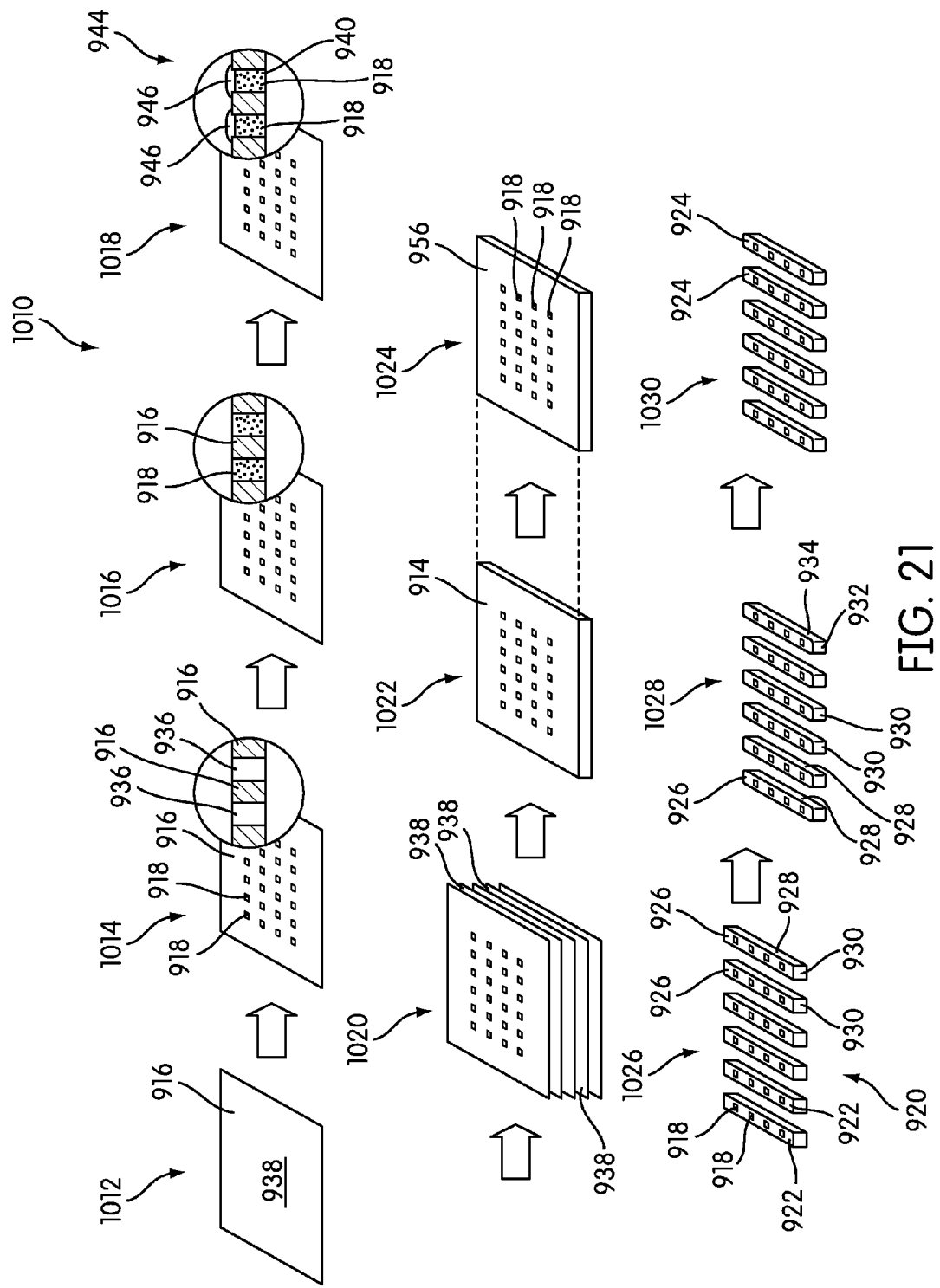
FIG. 21 is a perspective view of a process of manufacturing a feedthrough according to an exemplary embodiment.

Referring to FIG. 21, a method 1010 of manufacturing a feedthrough 924 includes providing sheets 1012 of green or un-fired ceramic material, forming 1014 holes in the ceramic sheets, and filling 1016 the holes with a metallization or paste. In some embodiments, the method 1010 includes printing covers or pads over the holes and metallization. The method 1010 further includes stacking 1020 and laminating 1022 the sheets, and then co-firing 1024 the ceramic and metallization. The method 1010 still further includes providing finished feedthroughs 1030 by cutting 1026 the co-fired composition and rounding 1028 corners of the cut elements. The finished feedthroughs may then be brazed into a ferrule and used as a portion of an implantable medical device.

In some embodiments, the method 1010 includes co-firing 1024 a composition 914 (e.g., high-temperature co-fired ceramic, fired above 1000° C., such as about 1600° C.; low-temperature co-fired ceramic, fired below 1000° C.) that includes a material 916 that is an electrical insulator and a conduit(s) 918 configured to convey electricity through the electrical insulator material 916. The method 1010 further includes cutting 920 (e.g., dicing, wafering) the composition 914 to form a body 922 of a feedthrough 924. The insulator body 922 may then be processed 1028 to form rounded corners 934 bordering a flat end surface 932.

In some embodiments, the body 922 has a top 926, a bottom (opposite to the top 926), two sides 928 extending lengthwise along the body 922, and two sides 930 on ends of the body 922 (see also faces 416 of feedthrough 410 as shown in FIGS. 10-13). In some such embodiments, the two sides 930 on the ends of the body 922 include exterior flat surfaces 932. The method further includes rounding corners 934 between the two sides 928 extending lengthwise along the body 922 and the two sides 930 on the ends of the body 922. The corners 934 are rounded, but the two sides 930 on the ends of the body 922 maintain the flat surfaces 932 between the corners 934, providing 1030 the finished feedthrough.

Figure 17:
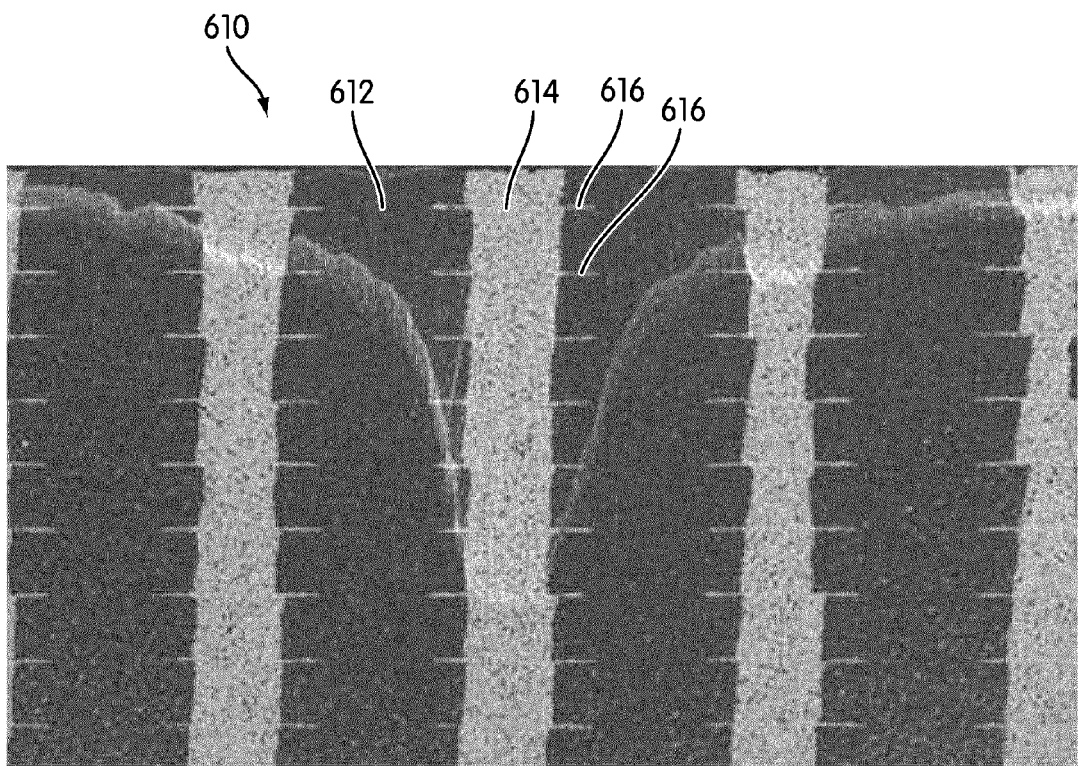
FIG. 17 is a sectional SEM micrograph of a portion of a feedthrough according to an exemplary embodiment.

In some embodiments, the method further includes filling holes 936 in sheets 938 of the electrical insulator material 916, where the holes 936 are filled with a conductive paste 940 used to form the conduit 918. Together, the sheets 938 and paste 940 are co-fired 1024 to form the feedthrough 924, typically after stacking and laminating of the sheets 938. The method 1010 further includes stacking 1020 the sheets 938 such that the holes 936 within each of the sheets 938 are substantially aligned with one another, forming a vertical path (see, e.g., conductive conduit 614 as shown in FIG. 17).

Figure 16:
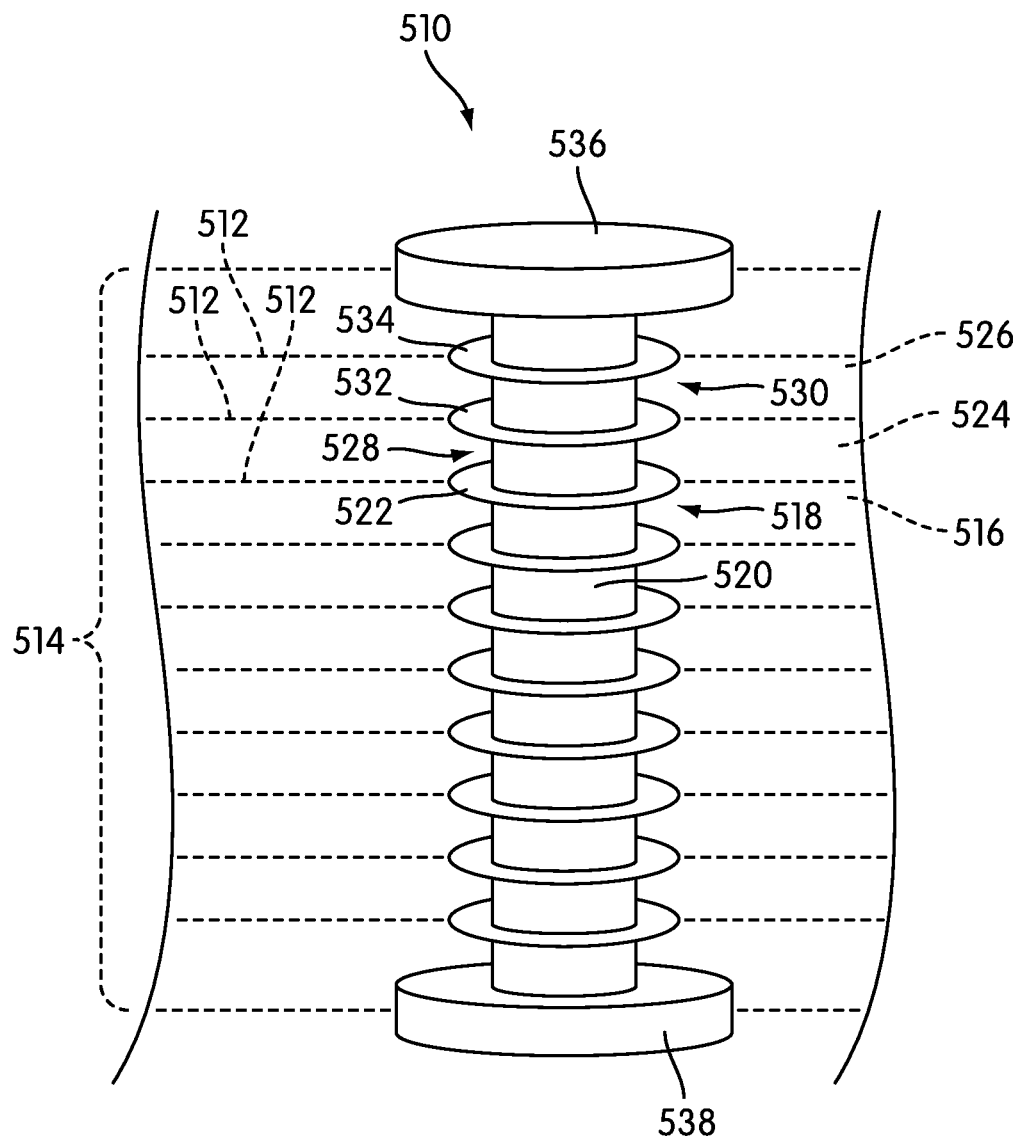
FIG. 16 is a perspective view of a conductor of a feedthrough according to an exemplary embodiment.

According to an exemplary embodiment, the method 1010 includes printing 944 a pad 946 overlaying the conduit 918. In some embodiments, the pad 946 may serve as an interconnect or top pad for the feedthrough 924, and may be formed from a series of layers printed over one another to increase the thickness of the pad 946 to a magnitude sufficiently thick to facilitate welding of a lead or wire to the pad 946 while maintaining the hermetic seal between the pad 946 and the body 922 of the feedthrough 924 (see also FIG. 19). In other embodiments, the pad 946 may serve as a cover pad to improve connectivity between conduits 918 of adjacent sheets 938 (see, e.g., cover pad 522 as shown in FIG. 16). In some embodiments, the sheets 938 include alumina or are mostly formed from alumina, the conductive paste 940 includes platinum and an additive, which may include alumina, and a layer of the pad 946 (e.g., cover pad and/or interconnect) is formed only of platinum.

Figure 13:
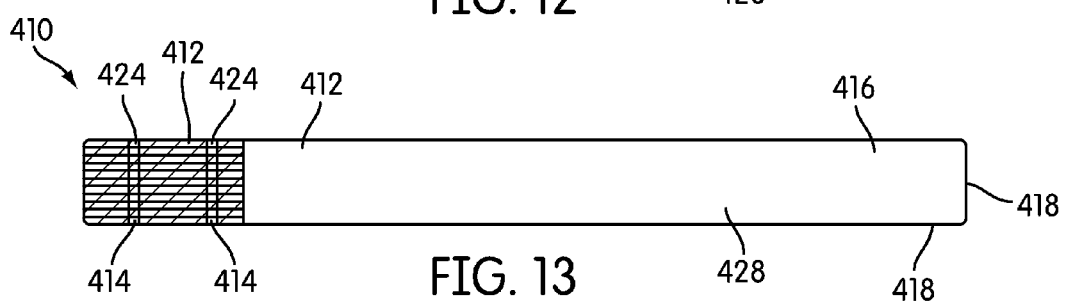
FIG. 13 is a side view and partial sectional view of the feedthrough of FIG. 4, where the sectional view is taken along line 13-13 in FIG. 11.

Referring now to FIG. 16, a feedthrough 510, which is configured to be used with an implantable medical device (see, e.g., devices 110, 210 as shown in FIGS. 1-2), includes a stack of sheets 512 (e.g., layers, ply, lamina, green sheets) that are laminated and fired together to form a single solid body 514 (see also sectional view of feedthrough 410 as shown in FIG. 13). At least one of the sheets 516 is formed from a first material, and has at least one hole 518 extending through the sheet 516. According to an exemplary embodiment, the first material of the sheet 516 is an electrical insulator material. A second material (e.g., metallization) substantially fills the hole 518, such as filling at least 75% of the volume of the hole 518 in contemplated embodiments. The second material is conductive or is configured to be conductive following firing, and forms an electrical conduit 520 through the sheet 516. In some such embodiments, the first material is a ceramic, which may include alumina, and the second material is different than the first material and may include platinum and an additive.

According to an exemplary embodiment, the sheet 516 of the first material and the conduit 520 of the second material have been co-fired with one another to at least partially form the feedthrough 510. The combination of first and second materials are selected to form a strong interface (e.g., co-fired bond) with one another. According to an exemplary embodiment, chem-mechanical bonding between the first and second materials is sufficient for the second material of the conduit 520 to hermetically seal the hole 518 in the sheet 516 of the first material as-fired, as-brazed, and after durability testing or implantation in a human. In some embodiments, the additive of the second material includes the first material (e.g., ceramic, alumina), which is intended to promote chem-mechanical co-fired bonding between the first and second materials during co-firing. In some such embodiments, the second material includes more platinum than alumina. In certain embodiments, the second material includes only platinum and alumina.

In at least some embodiments, the second material includes alumina, but does not include glass (or constituents thereof, such as $SiO_2$, MgO, CaO, crystalline oxides, or other constituents or glass) as an additive prior to co-firing. Typically glass is mixed with alumina to facilitate sintering of the alumina during firing. Typically glass is mixed with alumina to control sintering of the metallization during co-firing. However, it was discovered that glass is unnecessary to control sintering of the metallization when alumina is used as an additive for the second material. It is believed that the glass phase is drawn into the second material (e.g., diffuses) from the surrounding first material during co-firing, which is believed to provide an intermingling of materials along the interface, strengthening the chem-mechanical co-fired bond at the interface between the first and second materials (e.g., via walls). Furthermore, it was discovered that use of glass as an additive may actually decrease the effectiveness of the hermetic seal between the first and second materials, because the glass is believed to produce voids and other imperfections during firing of the second material, which may facilitate penetration of fluids through the second material or between the first and second materials of the feedthrough 510. In other contemplated embodiments, the second material may include glass.

Still referring to FIG. 16, the feedthrough 510 further includes a cover pad 522 (e.g., intra-layer pad, conductive disk, conduit extension) coupled to the sheet 516 and in electrical contact with the conduit 520. According to an exemplary embodiment, the cover pad 522 overlays the hole 518, and may extend at least partially over the sheet 516 past the hole 518. In other embodiments, cover pads are not included. In some embodiments, the cover pad 522 is formed from a third material (e.g., metallization) that is different than both the first and second materials. In other embodiments, the cover pad 522 is formed from the second material. The feedthrough 510 may also include external pads 536, 538 formed from a stacked structure that may include the second material and/or the third material. The third material is conductive and may include platinum. In some embodiments, the third material includes only platinum. In certain embodiments, the third material is more conductive than the second material. In other contemplated embodiments, the third material is the same as the second material.

According to an exemplary embodiment, the feedthrough 510 is formed from a combination of the sheets 512, which are stacked, laminated, and fired together. In some embodiments, the sheet 516 is a first sheet 516, and the feedthrough 510 further includes a second sheet 524 and a third sheet 526, and possibly more sheets 512. As discussed, the first sheet 516 is of the first material and has the hole 518, which is a first hole 518. The second and third sheets 524, 526 are also formed from the first material. The second sheet is bonded to the first sheet 516, and the third sheet 526 is fastened to the second sheet 524.

In such embodiments, the second sheet 524 has a second hole 528, and the third sheet 526 has a third hole 530. As discussed, the first hole 518 is filled with the second material, and according to an exemplary embodiment, the second and third holes 528, 530 are also filled with the second material. Furthermore, the first, second, and third holes 518, 528, 530 are vertically aligned with one another, in some embodiments, forming a substantially straight conductive path through the first, second, and third sheets 516, 524, 526. The first, second, and third holes 518, 528, 530 may substantially vertically overlap one another. In some such embodiments, the first and second materials of the feedthrough 510 have been co-fired such that a co-fired bond between the first and second materials hermetically seals the first, second, and third holes 518, 528, 530, despite the conductive path being substantially straight. Accordingly, the conductive path has improved conductivity when compared to tortuous paths of other feedthroughs, such as those of other embodiments.

According to an exemplary embodiment, the cover pad 522 is a first cover pad 522, and the feedthrough 510 further includes a second cover pad 532 and a third cover pad 534. The second and third cover pads 532, 534 respectively overlay the second and third holes 528, 530 and at least partially extend over the second and third sheets 524, 526, past the second and third holes 528, 530. In some such embodiments, a staggered conduit structure is contemplated, in which the first cover pad 522 overlaps at least a portion of (e.g., is adjacent to, fully overlaps) the first and second holes 518, 528, which are not directly aligned with one another in a vertical stack, and the second cover pad 532 overlaps the second and third holes 528, 530, which are also not directly aligned in a vertical stack. In other embodiments, the holes are directly aligned with one another in a vertical stack. According to an exemplary embodiment, the second and third cover pads 532, 534 are formed from the third material. In other embodiments the second and third cover pads 532, 534 are formed from the second material, or another material.

Referring now to FIG. 17, a section of an actual feedthrough 610, resembling the feedthrough 510, is shown in a scanning electron micrograph. The feedthrough 610 includes a body 612 formed from an insulator material, and a conductive conduit 614 extending through the body 612. The conduit 614 has been formed by filling holes in the sheets with a conductive material. The holes have been aligned with one another, and are capped by thin cover pads 616. According to an exemplary embodiment, the insulator material is a ceramic, including alumina; the conductive material includes a mixture of platinum and alumina; and the material of the cover pads 616 also includes a mixture of platinum and alumina. In other embodiments, the material of the pads 616 primarily includes platinum. The body 612 has been formed from a stack of sheets that have been laminated together and fired together in a kiln forming a co-fired bond therebetween. The materials have been co-fired together to form a hermetic seal preventing fluids from passing through the feedthrough 610.

Referring again to FIG. 21, another portion of the method 1010 of manufacturing a feedthrough includes providing 1012 the sheet 938 of first material 916, such as an electrical insulator material. In some embodiments, the sheet 938 is a ceramic that includes alumina. The method 1010 further includes forming 1014 (e.g., punching) at least one hole 936 in the first sheet 938, such as via a mechanical punch or press. In some embodiments, an array of holes 936 are punched into the sheet 938, such as a second hole and a third hole in addition to the first hole.

According to an exemplary embodiment, the method 1010 includes filling 1016 the hole 936 with the second material 940, which is different than the first material 916. In some embodiments, the second material 940 is conductive. In embodiments, with more than one hole 936, each of the holes 936 may be filled with the second material 940. When filling the hole 936, the second material 940 may be in the form of a paste, and may include platinum and an additive, such as alumina. The method 1010 includes co-firing 1024 the first and second materials 916, 940 such that a bond between the first and second materials 916, 940 hermetically seals the hole 936.

In some embodiments, the method 1010 may include providing additional sheets 938 of the first material 916 (e.g., second and third sheets), forming holes 936 in each of the additional sheets 938, and stacking 1020 the sheets 938. In some such embodiments, the sheets 938 are stacked such that corresponding holes 936 in the sheets 938 are vertically aligned with one another, forming a substantially straight conductive path through the first, second, and third sheets 938. The sheets 938 are then laminated 1022 to one another and co-fired 1024 such that the first and second materials 916, 940 form a solid composition 956 that is then cut or diced 1026 into individual bodies 922 that are hermetically sealed to prevent fluids from passing through the holes 936 or between the first and second materials 916, 940.

In some embodiments, the method 1010 includes printing 1018 pads 946 (e.g., cover pads) over the holes 936 and on the sheet 938, the pads 946 extend at least partially past the hole 936. In some such embodiments, the pads 946 may be formed from a third material that is different from the first and second materials 916, 936. In some embodiments, the third material includes platinum. In other such embodiments, the pads 946 may be formed from the second material 940. If multiple sheets 938 are used, and corresponding holes 936 between sheets 938 are vertically aligned, then the pads 946 may serve to improve electrical connectivity between the electrical conduits 918 of adjacent holes 936, especially if the holes 936 are not perfectly aligned with one another because of the larger diameter of the pads 946. In some such embodiments, the first, second, and third materials are co-fired together during the co-firing step 1024. In some embodiments, external or top pads may be printed over the conduits 918 or base pads of the laminated structure 914. The external pads may include a third material (e.g., metallization) that is different than both the first and second materials. The third material is conductive and may include platinum.

Figure 18:
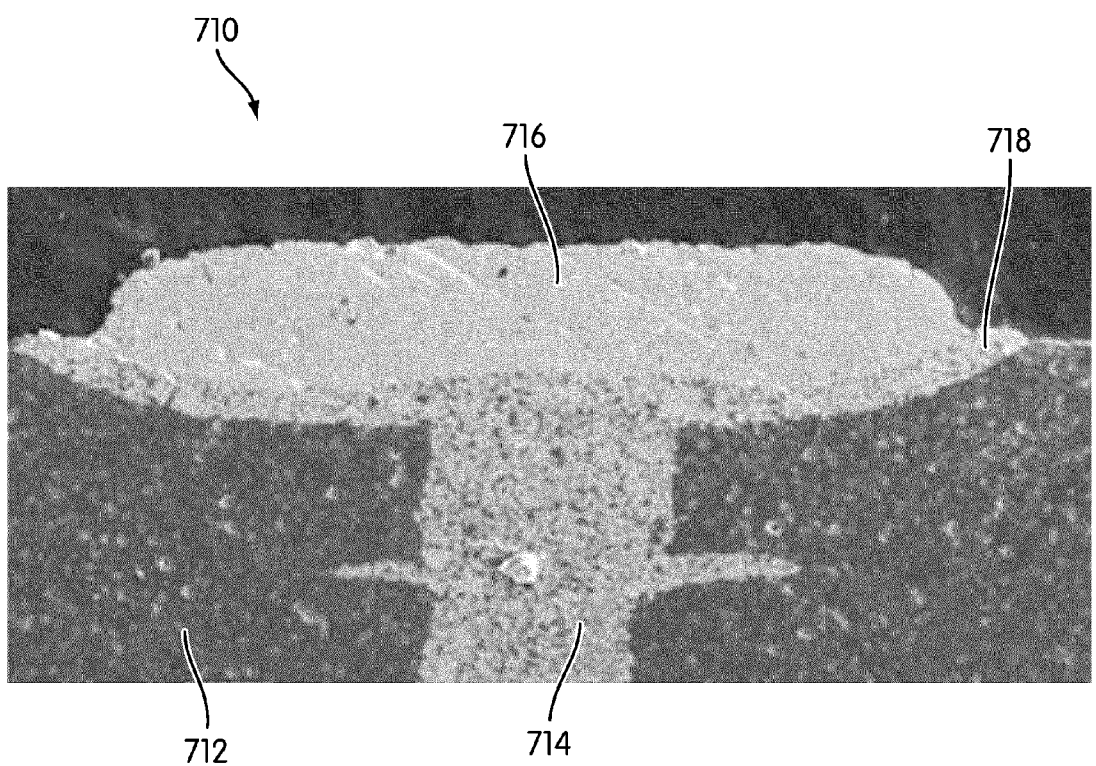
FIG. 18 is a sectional SEM micrograph of another portion of a feedthrough according to an exemplary embodiment.
Figure 19:
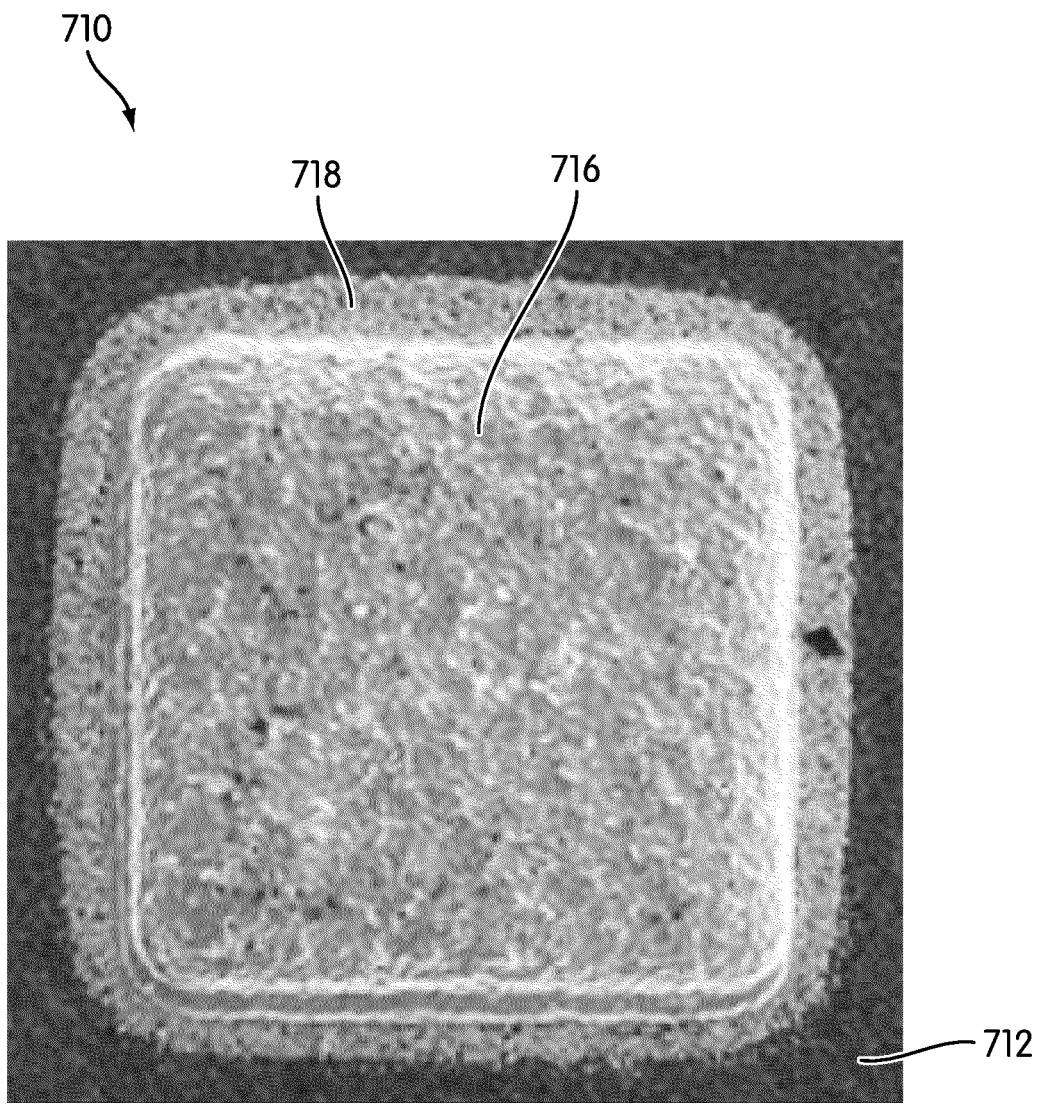
FIG. 19 is a top view SEM micrograph of a pad of a feedthrough according to an exemplary embodiment.

Referring now to FIGS. 18-19, a feedthrough 710 includes a body 712 (e.g., electrical insulator), a conduit 714 (e.g., via) extending through the body 712, and a pad 716 (e.g., top pad, base pad, interconnect) mounted to an exterior of the body 712, such as on a top or bottom surface of the body 712 and atop a base layer 718. According to an exemplary embodiment, the body 712 is formed from a first material that is an electrical insulator, and the conduit 714 is formed from a second material that is conductive. As such, the conduit 714 is configured to convey electricity through at least a portion of the body 712. The pad 716 is conductive and is electrically coupled to the conduit 714. According to an exemplary embodiment, the materials of the body 712, the conduit 714, and the pad 716 have been co-fired such that cohesion therebetween fastens and hermetically seals the pad 716 and the conduit 714 with the body 712, forming a continuous interface between the insulator body 712 and the pad 716, which is believed to be important for hermeticity. The continuous interface may also include coatings, the base layer 718 (e.g., under-layer), or other intermediate elements. In some embodiments, the feedthrough 710 includes a second pad coupled to the conduit 714 on an opposite side of the conduit (see, e.g., pads 536, 538 as shown in FIG. 16), which may be of different dimensions than the pad 716.

According to an exemplary embodiment, the pad 716 is sufficiently structured (e.g., with regard to thickness, material type, surface area, surface flatness, layering, etc.) so as to support welding of a lead or wire (e.g., Nb lead; cobalt-chromium-nickel alloy ("Co—Cr—Ni alloy," e.g., MP35N, 35N LT, Co—Cr—Ni alloy with nano-grain structure, ASTM standard F562)) to a top surface of the pad 716 without significantly damaging the hermetic seal between the pad 716 and the body 712. Many types of welding processes may be used including laser and parallel gap welding techniques. Some representative external interconnect techniques include laser welding, parallel gap welding, brazing, ultrasonic bonding, thermo-sonic bonding, soldering, diffusion bonding, and pressure or scraping contacts. Some representative external interconnect or lead materials include niobium, platinum, titanium, tantalum, palladium, gold and oxides and alloys thereof (e.g., $Ti_{15}Mo$, PtIr, Co—Cr—Ni alloy, Grade 36 TiNb alloy). Although shown as generally rectangular (e.g., square) in FIG. 19, in other contemplated embodiments the pad may be round or otherwise shaped. The shape may vary depending upon design requirements, while having upper layers of the pad 716 narrower than the base layer 718.

Figure 20:
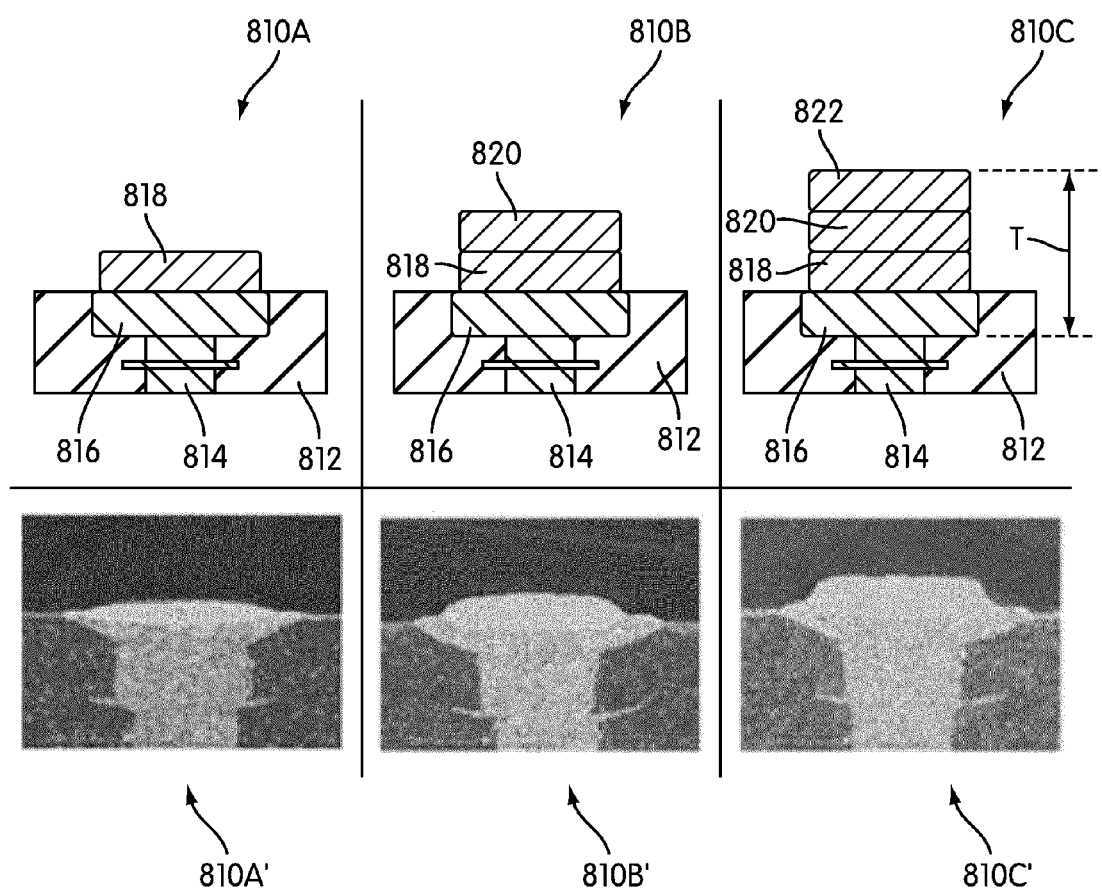
FIG. 20 is a series of sectional SEM micrographs and corresponding diagrams of portions of feedthroughs according to exemplary embodiments.

Referring now to FIG. 20, a pad 810 is coupled to an insulator 812 above a conductive conduit 814. According to an exemplary embodiment, from left to right FIG. 20 shows configurations of the pad 810 as the pad 810 is being constructed (e.g., printed), with the final form of the pad 810 shown in the configuration 810C on the right. The configurations 810A, 810B on the left and in the middle may be final forms of the pad 810 according to other embodiments. The lower row of FIG. 20 includes actual micrographs, provided by a scanning electron microscope, of three different pads 810A', 810B', and 810C' representative of the three configurations 810A, 810B, and 810C shown in the upper row of FIG. 20.

According to an exemplary embodiment, the pad 810 includes a first layer 816, and a second layer 818 overlaying at least a portion of the first layer 816. The insulator 812 is formed from a first material, the conduit 814 is formed from a second material, the first layer 816 of the pad 810 is from the second material, and, in some embodiments, the second layer 818 of the pad 810 is formed from a third material. According to an exemplary embodiment, the second material serves as an intermediary between the first and third materials to improve adhesion. In some embodiments, the first layer 816 of the pad 810 separates the second layer 818 of the pad 810 from the first material of the insulator 812 such that the second layer 818 of the pad 810 is not in direct contact with the first material. In some such embodiments, the first material includes alumina, the second material includes platinum with alumina as an additive, and the third material includes primarily platinum.

In some embodiments, the pad 810, which may include layers 820, 822 in addition to the first and second layers, has a thickness T of at least 50 μm, such as at least about 75 μm or about 100 μm. In some embodiments, the pad 810 is less than 200 μm thick. Such thickness T is believed sufficient to allow for forming of a molten bead of material to weld a lead or wire to the pad 810, without melting the conduit 814 or separating from the insulator 812. If the pad 810 is too thin, it has been found that thermal stresses may cause the pad 810 or conduit 814 to crack or delaminate from the insulator 812, damaging the connectivity of the associated feedthrough.

It is believed that interconnect pads for feedthroughs that are formed from platinum and are of a typical thickness on the order of 10 to 15 μm may be too thin to receive leads using standard welding processes (e.g., laser and parallel gap welding techniques), because it has been found that such pads deform or separate from the respective insulator, harming the hermetic seal of the feedthrough. Heat from the welding processes may also pass through such pads to melt the underlying conduit, harming the hermetic seal of the feedthrough. On the other hand, pads on the order of 10 to 15 μm (base pads) may be sufficiently thick for soldering, brazing, or wire bonding processes, in contrast to welding. But soldering or brazing processes and associated materials may not be biocompatible or biostable. With that said, in some contemplated embodiments a pad having a thickness less than 50 μm, such as on the order of 10 to 15 μm, or greater than 15 μm, may be used with certain pad materials or welding techniques. It should be noted that while the quantities and ranges provided herein may be useful in some configurations, in other configurations, such as those with other materials, geometries, used in other applications, etc., the quantities and ranges may be inapplicable, while the general teachings provided herein may still apply. For example, the dimensional thresholds of the pad may be based upon the particular details of the weld process evaluated, where if weld process configurations were changed; made larger/smaller, lower/higher power, etc., the dimensional thresholds would correspondingly change.

Still referring to FIG. 20, the pad 810C includes the third layer 820 on the second layer 818, and a fourth layer 822 on the third layer 820. In some such embodiments, the third and fourth layers 820, 822 are of the third material, and are printed on the second layer 818 to increase the thickness of the pad 810 so that the pad 810 is configured to receive a lead welded thereto. According to an exemplary embodiment, the fourth layer 822 is the top layer of the pad 810, and has a top surface area of more than 10×10 mil (i.e., ¹⁄₁₀₀ inch by ¹⁄₁₀₀ inch) in magnitude (e.g., may have circle, square, rectangle, or other shapes). In some embodiments, the top surface area is more than about 20×20 mil, such as about 30×30 mil or about 40×40 mil. Such a surface area on the top of the pad 810 is believed to be sufficiently large to allow for forming of a molten bead of material to weld a lead or wire to the pad, without melting sides of the pad 810 or separating the pad from the insulator 812, which would harm the hermetic seal. It is believed that the pads formed from platinum having surface areas that are less than about 30×30 mil may be too small to receive leads in some standard welding processes, because such pads have been found to melt and separate from the body, harming the hermetic seal of the feedthrough. However, in contemplated embodiments a pad having a surface area less than 30×30 mil may be used with certain pad materials or welding techniques. It should be noted that volumes and ranges of volumes of pads, according to various embodiments, include the product of any pad areas and any pad thicknesses disclosed herein, or the product of any pad lengths, widths, and thicknesses disclosed herein.

According to an exemplary embodiment, the surface of the top of the pad 810 is sufficiently flat so as to facilitate welding of a lead or wire to the surface. In some such embodiments, the top of the pad has a root mean square value of less than about 10 μm for flatness, such as less than about 7 μm for flatness, where the area measured for flatness corresponds to the center 50% of the top of the pad (e.g., central circle in circular pad, central rectangle in rectangular pad). In other contemplated embodiments, pads are designed to project vertically, forming a posting for connection of a lead or other interconnect. Parallel gap welding or laser welding may be used to fasten a lead to a posted protrusion.

Various conductive pastes reformulated from platinum powders may be used to form conductive features (e.g., conduit, pad) of feedthroughs in some embodiments. A first paste is formed from a first platinum powder consisting essentially of platinum having an average particle size distribution $d_{50}$ (mass-median-diameter in log-normal distribution) in the range of 3-10 μm ("Pt-1"). A second paste is formed from a second platinum powder consisting essentially of platinum having a coarser average particle size distribution $d_{50}$ in the range of 5-20 μm ("Pt-2"). A third paste is formed from a combination of about equal parts of the first and second platinum powders and about 2-10% by weight alumina (e.g., $Al_2O_3$), such as about 5% alumina. A fourth paste is formed from the first and second powders mixed together at a ratio of about 3:1 (e.g., 70-80%), respectively.

Mixing of the first and second powders in the third and fourth pastes is intended to control the sintering shrinkage and/or shrinking profile of the resulting metallization. In one example, paste formed from a 7:3 mixture of the first and second powders and about 5% alumina additive resulted in 13% shrinkage in thermo-mechanical analysis (TMA). In another example with the same mixture of first and second powders and about 7% alumina, the shrinkage was 12%. In another example, paste formed from a mixture of about equal parts of the first and second powders and about 5% alumina, resulted in 15% shrinkage, while the same mixture with 7% alumina resulted in 13% shrinkage.

By way of examples provided for context, various combinations of the pastes and numbers of layers have been constructed to test the qualities, such as top pad thickness and flatness, of the resulting pads following co-firing. In two such examples, a top layer of the second paste was printed atop a base layer of the third paste (e.g., "double printing") and co-fired, resulting in top pad thicknesses of 37 and 39 μm (e.g., average of 10-20 sample measurements per pad), respectively, and with root mean square (RMS) average flatness values of 4.2 and 3.9 μm, respectively (see generally pad 810A as shown in FIG. 20). In another example, a top layer of the first paste was printed atop a base layer of the third paste, which resulted in a top pad thickness of 130 μm and RMS average flatness value of 12.3 μm. In another two examples, two top layers of the second paste were printed atop a base layer of the third paste (e.g., "triple printing") and co-fired, resulting in top pad thicknesses of 55 and 59 μm, respectively, and with RMS average flatness values of 2.5 and 3.3 μm, respectively (see generally pad 810B as shown in FIG. 20). In yet another two examples, three top layers of the second paste were successively printed atop a base layer of the third paste (e.g., "quadruple printing") resulting in top pad thicknesses of 81 μm and RMS average flatness values of 3.9 and 4.2 μm, respectively (see generally pad 810C as shown in FIG. 20). In another example, three top layers of the first paste were successively printed atop a first layer of the third paste resulting in a pad thickness of 109 μm and an RMS average flatness value of 6.0. In still another example, three top layers of the fourth paste were successively printed atop a first layer of the third paste resulting in a pad thickness of 104 μm and an RMS average flatness value of 5.1, which resulted in a pad coupled to the underlying conductive conduit (of the third paste) and to the insulator without cracking or delamination. The net thickness of the top layers and base layer was 136 μm.

Various pad configurations were constructed using pastes formed from combinations of Pt-1 platinum powder, Pt-2 platinum powder, and platinum powder formed from equal parts of Pt-1 and Pt-2 ("Pt-3"). FIG. 20 shows examples of such configurations. The following table, provided for context, summarizes screening of various pad structures:

TABLE 9

| | | | | Structure | | |
|---|---|---|---|---|---|---|
| | | | | | Pt-2 | |
| | | | Pt-2 | Pt-2 | Pt-2 | Pt-1 |
| | Pt-2 | Pt-2 | Pt-2 | Pt-2 | Pt-2 | Pt-3 |
| | Pt-3 | Pt-3 | Pt-3 | Pt-3 | Pt-3 | Pt-3 |
| Thickness | 37 μm | 39 μm | 55 μm | 59 μm | 81 μm | 130 μm |
| Flatness | 4.2 μm | 3.9 μm | 2.5 μm | 3.3 μm | 3.9 μm | 12.3 μm | where the "Structure" row shows the layers of platinum paste in vertical order, the "Thickness" row shows the thickness of the top pad (above the Pt-3 layer), and the "Flatness" row shows the root mean square average flatness values. Platinum powder formed from three parts Pt-1 to one part Pt-2 ("Pt-4") was used and the pad structures were further refined, as summarized in the following table provided for context:

TABLE 10

| | Structure | | |
|---|---|---|---|
| | Pt-2 | Pt-1 | Pt-4 |
| | Pt-2 | Pt-1 | Pt-4 |
| | Pt-2 | Pt-1 | Pt-4 |
| | Pt-3 | Pt-3 | Pt-3 |
| Thickness | 81 μm | 109 μm | 104 μm |
| Flatness | 4.3 μm | 6.0 μm | 5.1 μm | where the rows match those of TABLE 9. The structure formed from quadruple printing of Pt-4 and Pt-3 layers showed no signs of cracking along the pad edge and showed relative flatness. In at least one embodiment, the top of the pad was formed by three stacked layers of Pt-4 with a base layer of the pad, and via (including intermediate cover pads) composed of Pt-3 with 5% alumina additive.

By way of examples provided for context, highly-accelerated immersion testing for dye infiltration at 150° C., 3.5 atm, for 30 days following a 1 hour, 500° C., vacuum pre-heating, was conducted on sample feedthroughs formed from various combinations of the pastes. Despite initial measurements indicating hermeticity before testing, during testing it was surprising to find evidence of loss of hermeticity (e.g., dye infiltration) in feedthroughs constructed with pads (e.g., top pad, main pad), cover pads (e.g., pads in between layers), and conduits (e.g., via) all formed from the first paste in alumina insulators, as well as those all formed from the first paste plus a lesser amount of alumina additive (e.g., about 2.5%). By contrast, no loss of hermeticity was found in feedthroughs constructed with pads, cover pads, and conduits formed from the first paste plus a greater amount of alumina additive (e.g., about 5% and about 7.5%). Also, no loss of hermeticity was found in feedthroughs constructed with pads and cover pads of the second paste and conduits (e.g., via) between the cover pads formed from paste formed from the first powder and 5% alumina additive. It is believed that using only alumina as an additive, as opposed to further including $SiO_2$, MgO, and CaO, decreases initial defects between the conduit and insulator.

The pad, in some embodiments, may be sufficient to maintain hermeticity and long-term biostability regardless of the composition and interface of the conductive conduit. In other embodiments, the pad may conduct electricity to the conduit, but may not be designed to prevent ingress of bodily fluids. In some such embodiments, the conductive conduit may be formulated and structured to provide a hermetic seal and long-term biostability to the feedthrough. It should be noted that improved reliability may be provided by pads and conductive conduits that together are redundantly hermetically-sealed and long-term biostable.

Referring once again to FIG. 21, a portion of the method 1010 of manufacturing a feedthrough 924 includes providing 1012 the sheet 938 or body of the first material 916. In some embodiments, the sheet 938 has a conduit 918 of a second material 940 extending through a hole 936 in the first material 916. The first material 916 is an electrical insulator and the second material 940 is conductive. The method 1010 further includes printing 1018 a first layer (see, e.g., first layer 816 as shown in FIG. 20 and base layer 718 as shown in FIGS. 18-19) of a pad 946 (e.g., interconnect, top pad) on the sheet 938. The first layer overlays the conduit 918 and is electrically coupled to the conduit 918. In some embodiments, the first layer of the pad 946 is formed from the second material 940.

According to an exemplary embodiment, the method further includes printing 1018 a second layer (see, e.g., second layer 818 as shown in FIG. 20) of the pad 946 on top of the first layer. The method further includes co-firing the sheet 938, the conduit 918, and the pad 946 such that cohesion therebetween fastens and hermetically seals the pad 946 and the conduit 918 with the sheet 938. Printing 1018 of multiple layers (see generally pad 810C as shown in FIG. 20) for the pad 946 allows for increased thickness of the pad 946, as may facilitate welding of a lead or wire to the pad while maintaining a hermetic seal between the pad 946, the conduit 918, and the sheet 938. Control of the dimensions of the pad 946 by printing 1018 multiple overlapping layers of the pad 946 allows for formation of a pad configured for use with an implantable medical device, because the pad 946 may be formed from biocompatible and biostable materials (e.g., platinum) arranged to be thick enough, wide enough, and flat enough for welding, while maintaining a hermetic seal with the body of the feedthrough 924.

While teachings disclosed herein relate generally to implantable medical devices (see, e.g., devices 110, 210 as shown in FIGS. 1-2), the disclosure is not intended to be limited to such devices. For example, some of the teachings disclosed herein relate to methods and structures that provide for a hermetic feedthrough, formed from a co-firing process. On a micro-scale, features that allow for a hermetic seal that remains biostable over a long duration (e.g., years), also provide strong, reliable bond between the insulator and the conductive components of the feedthrough. Such improved bond may be beneficial for non-medical, non-implantable devices undergoing conditions requiring high reliability and/ or long-term hermeticity for the components of a feedthrough, such as computers that experience large changes in temperature, operate in chemically aggressive environments, electrical devices that experience relatively high vibratory loading (e.g., aircraft electronics), high-value devices robustly constructed, and other devices.

In implantable medical device applications, it may be desirable to employ implantable medical devices, including portions thereof (e.g., feedthroughs), that are non-magnetic and are compatible with diagnostic tools that utilize magnetic fields, such as magnetic resonance imaging (MRI) systems. In some embodiments, the platinum and alumina materials, compositions, pastes, etc. disclosed herein (e.g., via paste, insulator material, pad material) are non-magnetic and are compatible with MRI and other magnetic diagnostic techniques.

The construction and arrangements of the feedthrough, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A method of manufacturing a feedthrough, comprising:
providing a ferrule having an opening;
providing an insulator body, including:
co-firing a structure comprising:
a material that is an electrical insulator; and
a conduit configured to conduct electricity through the electrical insulator;
cutting the structure to form the insulator body, wherein the insulator body includes a plurality of flat surfaces and a plurality of corners, each corner being positioned between two of the flat surfaces, wherein the plurality of flat surfaces include a pair of flat ends positioned at opposing ends of the insulator body along a longitudinal axis thereof;
inserting the insulator body into the opening of the ferrule; and
coupling the insulator body to the ferrule;
wherein the pair of flat ends of the insulator body are not ground before inserting the insulator body into the opening of the ferrule, and wherein the pair of flat ends are not machined or polished before inserting the insulator body into the opening of the ferrule.

2. The method of claim 1, wherein during the step of providing an insulator body includes rounding the corners of the insulator body before inserting the insulator body into the opening of the ferrule.

3. A method of manufacturing feedthrough, comprising:
providing a ferrule having an opening;
cutting a fired ceramic material to form an insulator body having a plurality of flat surfaces and a plurality of corners, each corner being positioned between two of the flat surfaces, wherein the plurality of flat surfaces include a pair of flat ends positioned at opposing ends of the insulator body along a longitudinal axis thereof;
inserting the insulator body into the opening of the ferrule; and
coupling the insulator body to the ferrule;
wherein the pair of flat ends of the insulator body are not ground before inserting the insulator body into the opening of the ferrule, and wherein the pair of flat ends are not machined or polished before inserting the insulator body into the opening of the ferrule.

4. The method according to claim 3, further comprising rounding the corners of the insulator body before inserting the insulator body into the opening of the ferrule.

5. The method according to claim 4, wherein the step of rounding the corners includes tumbling the insulator body in an abrasive agent.

6. The method according to claim 3, wherein the step of cutting the fired ceramic material utilizes a wafering saw.

7. The method according to claim 6, wherein the wafering saw includes one or more diamond cutting blades.

8. The method according to claim 3, wherein the step of cutting the fired ceramic material results in the insulator body having a rectilinear shape.

9. The method according to claim 3, further comprising brazing the insulator body to the ferrule.

10. The method according to claim 3, further comprising providing the fired ceramic material by:
providing a sheet of unfired ceramic material;
forming one or more holes through the unfired ceramic material;
inserting a first conductive material into the one or more holes;

forming a pad in electrical contact with the first conductive material in one of the plurality of holes, the pad comprising a second conductive material; and co-firing the unfired ceramic material, the first conductive material, and the second conductive material.

11. The method according to claim 10, wherein the step of forming the pad includes providing a plurality of layers overlaying each other to form the pad with a thickness of at least 50 micrometers, at least one layer comprising the second material.

12. The method according to claim 10, wherein the ceramic material comprises alumina, the first conductive material is different than the ceramic material and comprises alumina and platinum, and the second conductive material is different than the ceramic material and the first conductive material and comprises platinum.

13. The method according to claim 10, wherein providing the fired ceramic material further includes providing a second sheet of unfired ceramic material having one or more holes therethrough, inserting the first conductive material into the one or more holes of the second sheet, layering the second sheet with the first sheet with the one or more holes thereof in alignment; and wherein the step of co-firing includes co-firing the unfired ceramic material of the first sheet, the unfired ceramic material of the second sheet, the first conductive material, and the second conductive material.

14. The method according to claim 10, wherein the step of co-firing creates a hermetic seal between the unfired ceramic material and the first conductive material and between the first conductive material and the second conductive material.

15. The method according to claim 10, further comprising welding a lead to the pad subsequent to inserting the insulator into the ferrule.

* * * * *